United States Patent

Yoshino et al.

(10) Patent No.: US 8,767,058 B2
(45) Date of Patent: Jul. 1, 2014

(54) IMAGE PROCESSING APPARATUS, IMAGING APPARATUS, COMPUTER-READABLE STORAGE MEDIUM, AND IMAGE PROCESSING METHOD

(75) Inventors: Koichiro Yoshino, Tokyo (JP); Hiroshi Suzuki, Hachioji (JP)

(73) Assignee: Olympus Corporation, Tokyo (JP)

( * ) Notice: Subject to any disclaimer, the term of this patent is extended or adjusted under 35 U.S.C. 154(b) by 268 days.

(21) Appl. No.: 13/242,832

(22) Filed: Sep. 23, 2011

(65) Prior Publication Data

US 2012/0013773 A1    Jan. 19, 2012

Related U.S. Application Data

(63) Continuation of application No. PCT/JP2010/051418, filed on Feb. 2, 2010.

(30) Foreign Application Priority Data

Mar. 26, 2009 (JP) .................................. 2009-077562

(51) Int. Cl.
*A62B 1/04* (2006.01)
*G06K 9/00* (2006.01)
*A61B 1/06* (2006.01)

(52) U.S. Cl.
USPC .............................. 348/65; 382/294; 600/180

(58) Field of Classification Search
CPC ........ A61B 1/07; A61B 1/045; A61B 1/0638; H04N 2005/2255; H04N 5/2354; H04N 7/183; G06T 7/0028; G06T 7/0026; G06T 5/50; G06T 7/0024; G06K 9/32
USPC ............................. 348/271; 382/294; 600/180
See application file for complete search history.

(56) References Cited

U.S. PATENT DOCUMENTS

| 5,590,170 A | 12/1996 | Zweig | |
|---|---|---|---|
| 2005/0111758 A1 | 5/2005 | Lange et al. | |
| 2006/0025692 A1* | 2/2006 | Ishihara | 600/478 |
| 2007/0147705 A1* | 6/2007 | Clune et al. | 382/294 |
| 2009/0160386 A1 | 6/2009 | Honda et al. | |
| 2010/0177180 A1* | 7/2010 | Yamaguchi et al. | 348/65 |

FOREIGN PATENT DOCUMENTS

| JP | 07-250804 | 10/1995 |
|---|---|---|
| JP | 2002-074330 | 3/2002 |
| JP | 2002-336187 A | 11/2002 |
| JP | 2003-070008 | 3/2003 |

(Continued)

OTHER PUBLICATIONS

International Search Report dated Mar. 2, 2010 issued in PCT/JP2010/051418.

(Continued)

*Primary Examiner* — Dave Czekaj
*Assistant Examiner* — Tsion B Owens
(74) *Attorney, Agent, or Firm* — Scully, Scott, Murphy & Presser, P.C.

(57) ABSTRACT

An image processing apparatus includes a motion vector calculator and an alignment processing unit. The motion vector calculator calculates motion vector information between a fluorescence image of an observed region based on fluorescence generated from the observed region irradiated with excitation light, and a reflected-light image of the observed region based on reflected light from the observed region. The alignment processing unit corrects misalignment of an object between the fluorescence image and the reflected-light image of the observed region based on the motion vector information.

13 Claims, 17 Drawing Sheets

(56) References Cited

FOREIGN PATENT DOCUMENTS

| | | |
|---|---|---|
| JP | 2004-329514 | 11/2004 |
| JP | 2007-229053 | 9/2007 |
| JP | 2007-244746 A | 9/2007 |
| JP | 2008-183349 | 8/2008 |
| JP | 2009-160386 | 7/2009 |
| WO | 2008/093746 A1 | 8/2008 |

OTHER PUBLICATIONS

Japanese Office Action dated Oct. 30, 2012 from corresponding Japanese Patent Application No. 2009-077562, together with an English language translation.
Extended Supplementary European Search Report dated Feb. 24, 2014 from related European Application No. 10 75 5751.4.
US 6,692,429, 02/2004, Imaizumi et al. (withdrawn)

* cited by examiner

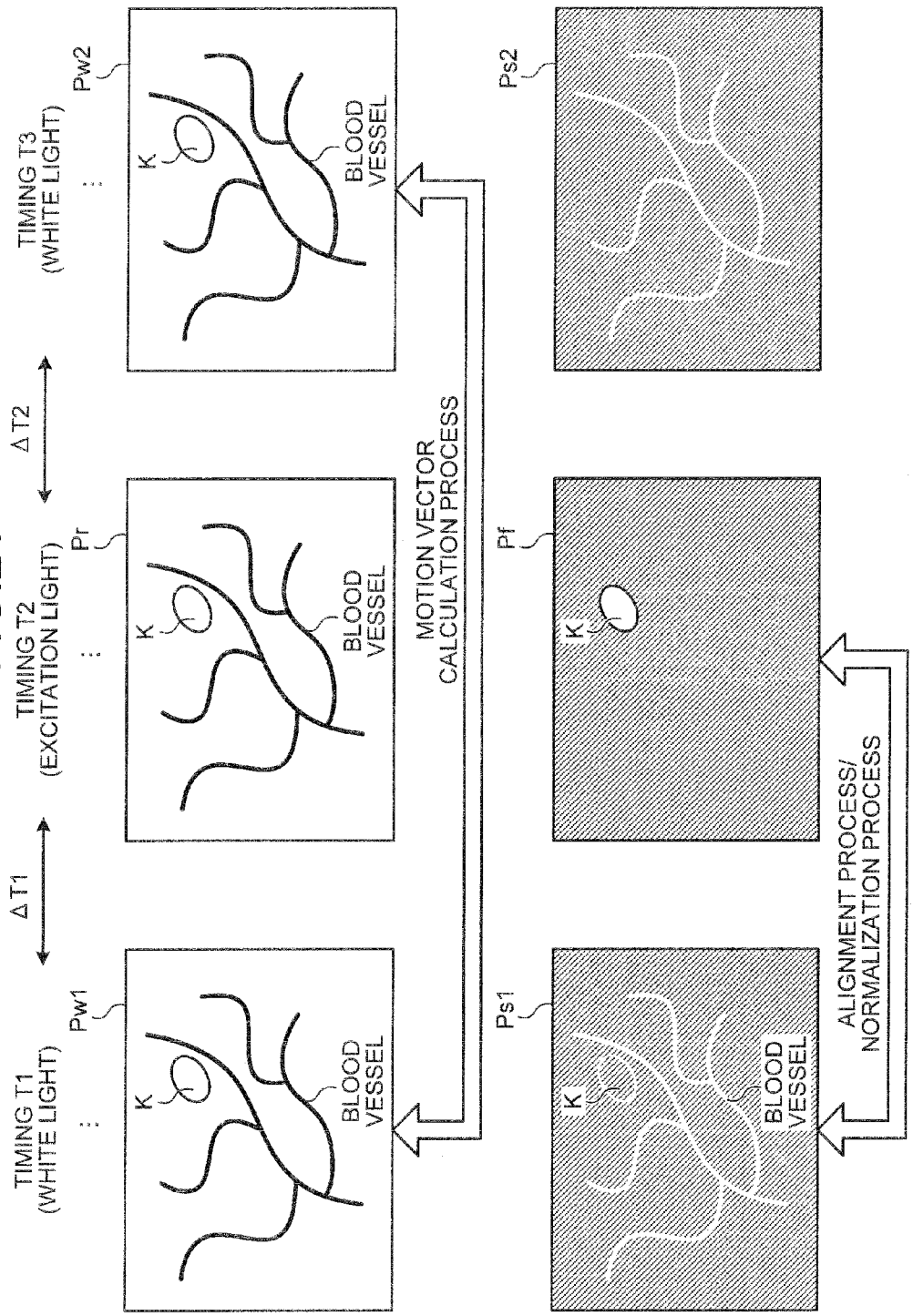

IMAGE PROCESSING APPARATUS, IMAGING APPARATUS, COMPUTER-READABLE STORAGE MEDIUM, AND IMAGE PROCESSING METHOD

CROSS-REFERENCES TO RELATED APPLICATIONS

This application is a continuation of PCT international application Ser. No. PCT/JP2010/051418 filed on Feb. 2, 2010 which designates the United States, incorporated herein by reference, and which claims the benefit of priority from Japanese Patent Application No. 2009-077562, filed on Mar. 26, 2009, incorporated herein by reference.

BACKGROUND OF THE INVENTION

1. Field of the Invention

The present invention relates to an image processing apparatus, an imaging apparatus, and an image processing method, and in particular to an image processing apparatus, an imaging apparatus, and an image processing method for processing a fluorescence image based on fluorescence from an object.

2. Description of the Related Art

Conventionally, in the medical field, endoscope systems are used when an inside of an organ of a subject is observed. In such an endoscope system, typically, a flexible insertable unit in an elongated shape is inserted into a body cavity of a subject such as a patient, a living tissue in the body cavity is irradiated with white light by the flexible insertable unit thus inserted, and reflected light thereof is received by an imaging unit in the flexible insertable unit, thereby capturing a white-light image of the living tissue. Such a white-light image of the living tissue is displayed on a display unit of the endoscope system. A user such as a doctor observes the inside of the body cavity of the subject through the white-light image of the living tissue displayed on the display unit of the endoscope system.

By contrast, in the field of endoscopes in recent years, an endoscope system is developed in which a living tissue in a body cavity is irradiated with excitation light other than white light by a flexible insertable unit inserted into the body cavity, and autofluorescence or drug-induced fluorescence generated from the living tissue based on the irradiation of the excitation light is received by an imaging unit in the flexible insertable unit, thereby capturing a fluorescence image of the living tissue (e.g., Japanese Laid-open Patent Publication No, 2007-229053). Furthermore, another endoscope system is developed in which a drug-induced fluorescence image of a lesion is captured based on drug-induced fluorescence generated from the lesion serving as an object, and the brightness of the drug-induced fluorescence image thus captured is normalized, thereby correcting the intensity of the fluorescence attributed to differences in the distance from the object to the imaging unit (e.g., Japanese Laid-open Patent Publication No. 2008-183349). The image processing apparatus of the endoscope system disclosed in Japanese Laid-open Patent Publication No. 2008-183349 acquires a drug-induced fluorescence image and an autofluorescence image of a target region to be observed in the body cavity sequentially, generates a normalization image based on the autofluorescence image, and divides the brightness value of the drug-induced fluorescence image by the brightness value of the normalization image, thereby normalizing the brightness of the drug-induced fluorescence image.

SUMMARY OF THE INVENTION

An image processing apparatus according to an aspect of the present invention includes a motion vector calculator that calculates motion vector information between a fluorescence image of an observed region based on fluorescence generated from the observed region irradiated with excitation light, and a reflected-light image of the observed region based on reflected light from the observed region; and an alignment processing unit that corrects misalignment of an object between the fluorescence image and the reflected-light image based on the motion vector information.

An imaging apparatus according to another aspect of the present invention includes a light source unit that switches normal light and excitation light, and irradiates an observed region therewith; a reflected-light imaging unit that receives reflected light from the observed region irradiated with the normal light, and captures a reflected-light image of the observed region; a fluorescence imaging unit that receives fluorescence generated from the observed region irradiated with the excitation light, and captures a fluorescence image of the observed region; a motion vector calculator that calculates motion vector information between the fluorescence image and the reflected-light image; and an alignment processing unit that corrects misalignment of an object between the fluorescence image and the reflected-light image based on the motion vector information.

A computer-readable storage medium according to still another aspect of the present invention has an executable program stored thereon, wherein the program instructs a processor to perform: calculating motion vector information between a fluorescence image of an observed region based on fluorescence generated from the observed region irradiated with excitation light, and a reflected-light image of the observed region based on reflected light from the observed region; and correcting misalignment of an object between the fluorescence image and the reflected-light image based on the motion vector information.

An image processing method according to still another aspect of the present invention includes calculating motion vector information between a fluorescence image of an observed region based on fluorescence generated from the observed region irradiated with excitation light, and a reflected-light image of the observed region based on reflected light from the observed region; and correcting misalignment of an object between the fluorescence image and the reflected-light image based on the motion vector information.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 21 is a schematic for specifically explaining operations performed by an image processing apparatus according to the fourth embodiment.

DETAILED DESCRIPTION OF THE PREFERRED EMBODIMENTS

Preferred embodiments of an image processing apparatus, an imaging apparatus, an image processing program, and an image processing method according to the present invention will be described below with reference to the accompanying drawings. In the description below, as an example of the imaging apparatus according to the present invention, an endoscope apparatus that captures an in-vivo image of a subject such as a patient is explained, and an image processing apparatus, an image processing program, and an image processing method used for the endoscope apparatus are explained. However, the present invention is not limited to the embodiments.

First Embodiment

Figure 1:
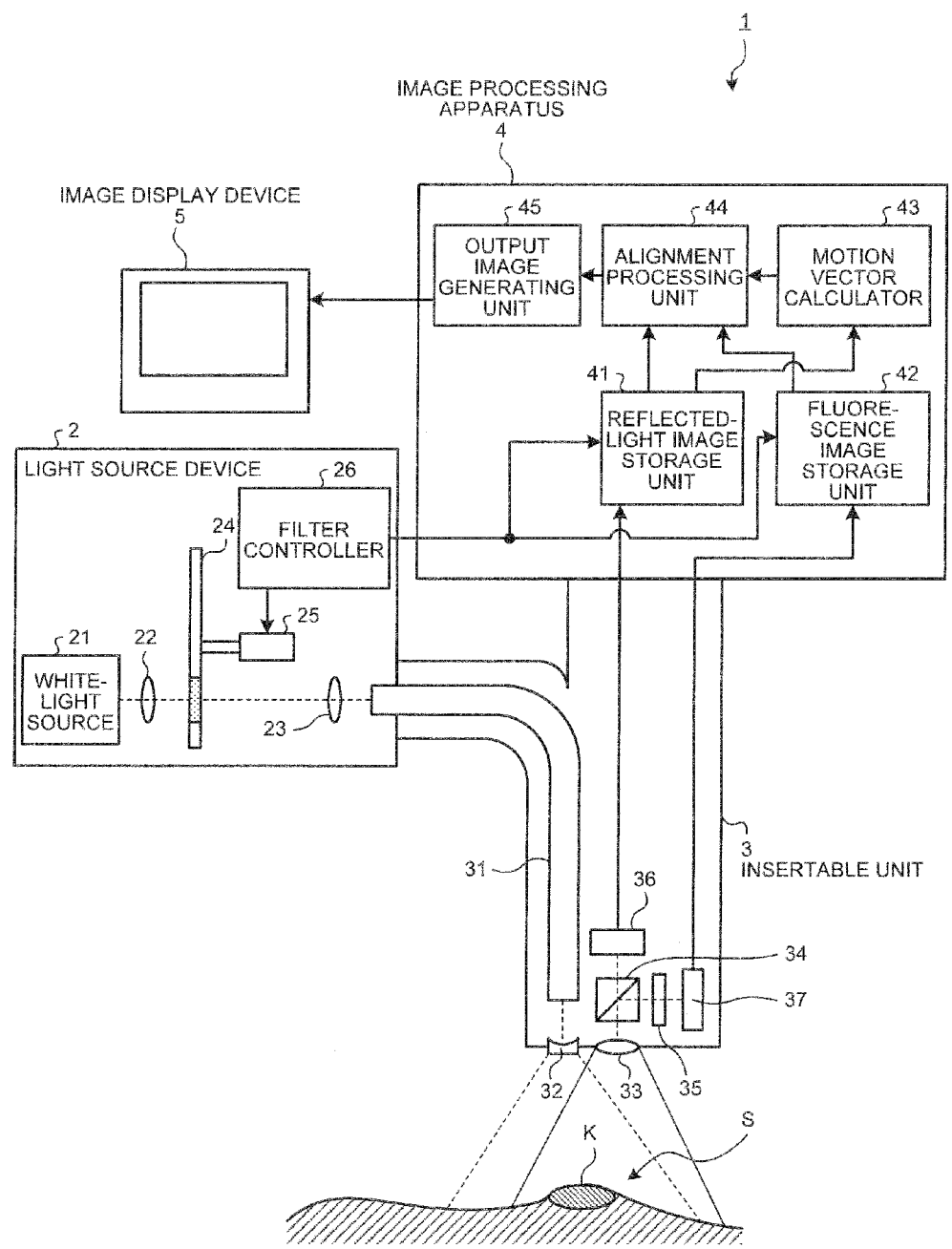
FIG. 1 is a block diagram schematically illustrating an exemplary configuration of an endoscope apparatus according to a first embodiment of the present invention.

FIG. 1 is a block diagram schematically illustrating an exemplary configuration of an endoscope apparatus according to a first embodiment of the present invention. An endoscope apparatus 1 according to the first embodiment is an example of the imaging apparatus according to the present invention, and includes a light source device 2 that irradiates an observed region S in a subject with light, an insertable unit 3 in an elongated shape inserted into a body cavity of the subject, an image processing apparatus 4 that processes an image of the observed region S, and an image display device 5 that displays image information processed by the image processing apparatus 4 as illustrated in FIG. 1.

The light source device 2 functions as a light source unit that switches excitation light that excites a fluorescent agent, and normal light such as white light to irradiate the observed region S therewith. Specifically, the light source device 2 includes a white-light source 21, a collimating lens 22 that makes light output from the white-light source 21 into approximately parallel light, a condenser lens 23 that condenses the parallel light, a rotating filter 24 that switches the excitation light and the normal light as light with which the observed region S is irradiated, a motor 25 that is a driving source of the rotating filter 24, and a filter controller 26 that controls the rotating filter 24.

The white-light source 21 is a light emitting source of the light source device 2, and emits white light based on operations of a switch (not illustrated) of the light source device 2. The collimating lens 22 is arranged on an optical path of the white light output from the white-light source 21, and makes the white light from the white-light source 21 into approximately parallel light. The parallel light collimated by the collimating lens 22 passes through the rotating filter 24, and is condensed again by the condenser lens 23. With the light condensed by the condenser lens 23, the observed region S in the subject is irradiated by the insertable unit 3.

Figure 2:
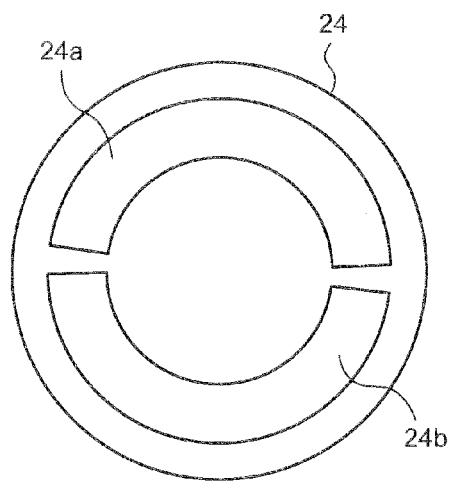
FIG. 2 is a schematic illustrating an exemplary configuration of a rotating filter.
Figure 3:
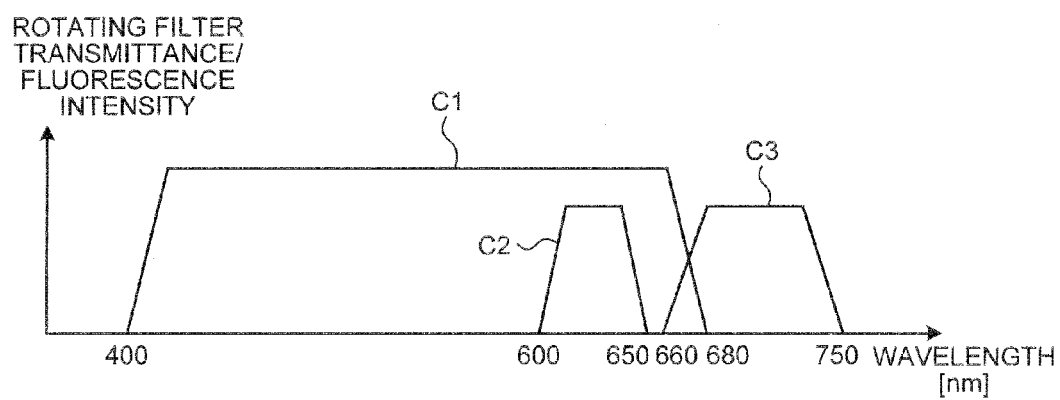
FIG. 3 is a schematic illustrating an example of transmittance characteristics of the rotating filter.

The rotating filter 24 extracts light at a predetermined wavelength band from the white light emitted by the white-light source 21. FIG. 2 is a schematic illustrating an exemplary configuration of the rotating filter. FIG. 3 is a schematic illustrating an example of transmittance characteristics of the rotating filter. In FIG. 3, intensity characteristics of fluorescence generated by excitation light extracted by the rotating filter 24 are illustrated, as well. As illustrated in FIG. 2, the rotating filter 24 includes a white-light filter 24a and an excitation-light filter 24b that have different transmittance characteristics.

The white-light filter 24a is a filter that transmits the white light, and has transmittance characteristics that transmit light at a wavelength band of 400 to 680 nm as indicated by a correlation line C1 of transmittance versus wavelength illustrated in FIG. 3. The white-light filter 24a transmits the white light from the white-light source 21 as the normal light with which the observed region S is irradiated. The excitation-light filter 24b is a filter that transmits the excitation light, and has transmittance characteristics that transmit light at a wavelength band of 600 to 650 nm as indicated by a correlation line C2 of the transmittance versus wavelength illustrated in FIG. 3. The excitation-light filter 24b extracts the excitation light that is light at a wavelength band of 600 to 650 nm from the white light from the white-light source 21, and transmits the excitation light thus extracted.

The excitation light extracted by the excitation-light filter 24b has characteristics that, for example, excite the fluorescent agent accumulated specifically in a lesion K such as a tumor in the observed region S, and cause the agent to generate fluorescence at a wavelength band of 660 to 750 nm (refer to a correlation line C3 illustrated in FIG. 3).

The rotating filter 24 including the white-light filter 24a and the excitation-light filter 24b is rotated in the circumferential direction by the drive of the motor 25, thereby switching the white-light filter 24a and the excitation-light filter 24b so as to be positioned in the optical path (refer to a dashed line in the light source device 2 illustrated in FIG. 1) of the white light from the white-light source 21 sequentially. The rotating filter 24 transmits the white light with the white-light filter 24a being positioned in the optical path, and transmits the excitation light with the excitation-light filter 24b being positioned in the optical path. In other words, the rotating filter 24 transmits the white light and the excitation light alternately.

The filter controller 26 controls the switching of the filters in the optical path by the rotation of the rotating filter 24. Specifically, the filter controller 26 controls rotary drive of the motor 25 connected to the rotating filter 24 via a rotating shaft, and controls rotary drive of the rotating filter 24 through the drive control of the motor 25. Thus, the filter controller 26 causes the white-light filter 24a and the excitation-light filter 24b to be positioned in the optical path of the white light from the white-light source 21 alternately at time intervals specified in advance. In this manner, the filter controller 26 controls the switching of the filters of the rotating filter 24 in the optical path. The filter controller 26 recognizes whether the white-light filter 24a or the excitation-light filter 24b is positioned in the optical path based on the rotary drive state of the motor 25, such as the rotation speed thereof. The filter controller 26 transmits filter information indicating the filter (the white-light filter 24a or the excitation-light filter 24b) positioned in the optical path to the image processing apparatus 4.

The insertable unit 3 is a flexible structure in an elongated shape that is insertable into the body cavity of the subject, and is capable of bending in a desired direction based on operations of an operating unit (not illustrated) of the endoscope apparatus 1. As illustrated in FIG. 1, the insertable unit 3 includes a light guide fiber 31 whose proximal end portion is connected to the light source device 2 and the image processing apparatus 4, and that guides the light output from the light source device 2 to a distal end portion thereof, and a lens 32 that diffuses the light guided by the light guide fiber 31. The insertable unit 3 includes an objective lens 33 that condenses reflected light or fluorescence from the observed region S, a dichroic mirror 34 that separates the light condensed from the observed region S, and a barrier filter 35 that transmits the fluorescence and blocks the excitation light from the observed region S. Furthermore, the insertable unit 3 includes a reflected-light imaging unit 36 that captures a reflected-light image of the observed region S, and a fluorescence imaging unit 37 that captures a fluorescence image of the observed region S.

The light guide fiber 31 is realized by using an optical fiber or the like, and propagates the white light and the excitation light output from the light source device 2 alternately at the predetermined time intervals to the distal end portion of the insertable unit 3 sequentially. The white light and the excitation light from the light source device 2 guided by the light guide fiber 31 sequentially are diffused by the lens 32 sequentially, such that the observed region S in the subject is irradiated therewith alternately at the time intervals specified in advance.

If the lesion K in which the fluorescent agent is accumulated in advance is present in the observed region S, the excitation light from the light source device 2 with which the observed region S is irradiated excites the fluorescent agent in the lesion K, and causes the agent to generate fluorescence at a wavelength hand of 660 to 750 nm, for example. By contrast, if the observed region S is irradiated with the white light from the light source device 2, the white light is reflected from the observed region S.

If the observed region S is irradiated with the white light from the light source device 2, the objective lens 33 condenses the white light reflected from the observed region S. By contrast, if the observed region S is irradiated with the excitation light from the light source device 2, the objective lens 33 condenses the fluorescence generated from the observed region S (specifically, the fluorescence generated from the lesion K), and the excitation light reflected from the observed region S. Among the light from the observed region S condensed by the objective lens 33, the dichroic mirror 34 separates the reflected light of the white light, the excitation light, and the like reflected from the observed region S into an optical path on the reflected-light imaging unit 36 side, and separates the fluorescence generated from the observed region S and a part of the reflected light from the observed region S into an optical path on the fluorescence imaging unit 37 side.

Figure 4:
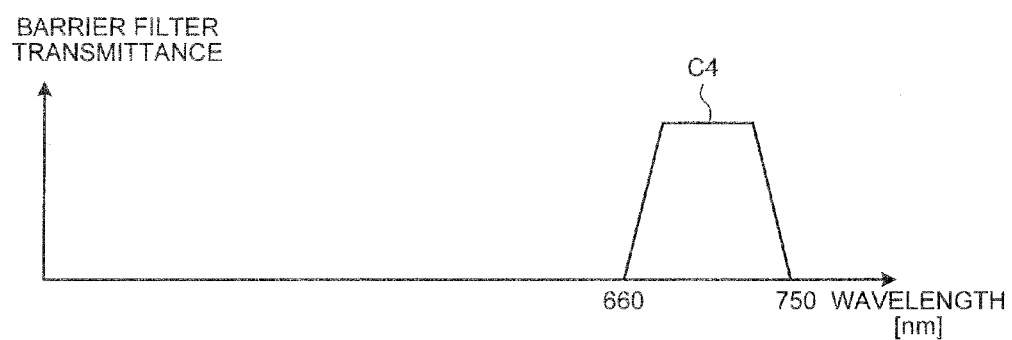
FIG. 4 is a schematic illustrating an example of transmittance characteristics of a barrier filter in the first embodiment of the present invention.

The barrier filter 35 is a filter for blocking the reflected light of the excitation light and the like included in the light from the observed region S separated into the optical path on the fluorescence imaging unit 37 side by the dichroic mirror 34. FIG. 4 is a schematic illustrating an example of transmittance characteristics of the barrier filter in the first embodiment of the present invention. As indicated by a correlation line C4 of transmittance versus wavelength illustrated in FIG. 4, the barrier filter 35 has transmittance characteristics that transmit light at a wavelength band of 660 to 750 nm. Among the light from the observed region S separated into the optical path on the fluorescence imaging unit 37 side by the dichroic mirror 34, the barrier filter 35 blocks the reflected light from the observed region S, and transmits the fluorescence, which is light at a wavelength band of 660 to 750 nm, from the observed region S.

Figure 5:
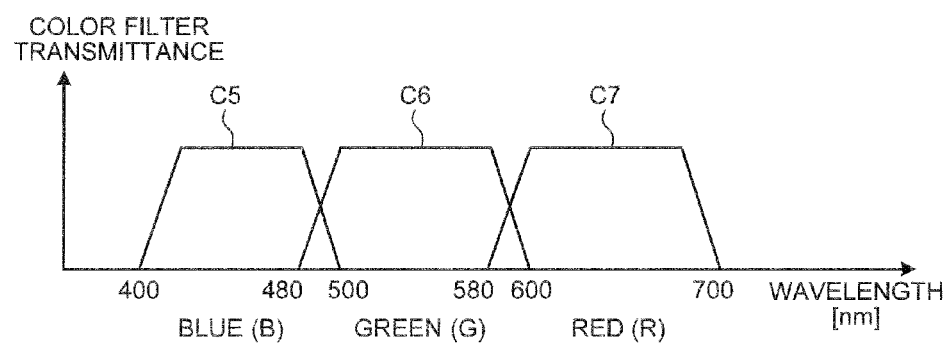
FIG. 5 is a schematic illustrating an example of spectral characteristics of a plurality of color filters arranged in a reflected-light imaging unit.

The reflected-light imaging unit 36 is realized by using a Bayer-type color imaging element in which color filters are arranged for respective pixels in a photosensitive surface. FIG. 5 is a schematic illustrating an example of spectral characteristics of a plurality of color filters arranged in the reflected-light imaging unit. The reflected-light imaging unit 36 includes color filters of red (R), green (G), and blue (B), each of which is provided in plurality, and has transmittance characteristics illustrated in FIG. 5. As indicated by a correlation line C7 of transmittance versus wavelength illustrated in FIG. 5, the red color filter has transmittance characteristics that transmit light (R light) at a wavelength band of 580 to 700 nm. As indicated by a correlation line 56 of the transmittance versus wavelength illustrated in FIG. 5, the green color filter has transmittance characteristics that transmit light (G light) at a wavelength band of 480 to 600 nm. As indicated by a correlation line 55 of the transmittance versus wavelength illustrated in FIG. 5, the blue color filter has transmittance characteristics that transmit light (B light) at a wavelength band of 400 to 500 nm. The reflected-light imaging unit 36 receives the reflected light from the observed region S separated into the optical path on the reflected-light imaging unit 36 side by the dichroic mirror 34, and thus captures a reflected-light image, which is a color image of the observed region S. Specifically, when receiving the white light reflected from the observed region S, the reflected-light imaging unit 36 captures a reflected-light image (hereinafter, referred to as a white-light image of the observed region S in some cases) based on the white light from the observed region S. By contrast, when receiving the excitation light reflected from the observed region S, the reflected-light imaging unit 36 captures a reflected-light image (hereinafter, referred to as a reflected-excitation-light image of the observed region S in some cases) based on the excitation light from the observed region S at the same imaging timing as that of a fluorescence image of the observed region S captured by the fluorescence imaging unit 37, which will be described later. Every time the reflected-light imaging unit 36 captures the white-light image or the reflected-excitation-light image of the observed region S, the reflected-light imaging unit 36 transmits an image signal including the image information thus obtained to the image processing apparatus 4 sequentially.

The fluorescence imaging unit 37 is realized by using a monochrome imaging element having high sensitivity characteristics compared with the reflected-light imaging unit 36. The fluorescence imaging unit 37 receives the fluorescence from the observed region S separated into the optical path on the fluorescence imaging unit 37 side by the dichroic mirror 34, that is, receives the fluorescence passing through the barrier filter 35, and thus captures the fluorescence image of the observed region S. The intensity of the fluorescence in the fluorescence image of the observed region S captured by the fluorescence imaging unit 37 changes depending on the distance from the observed region S serving as the object to the fluorescence imaging unit 37. The fluorescence image of the observed region captured by the fluorescence imaging unit 37 is an image captured at the same timing as that of the reflected-excitation-light image of the observed region S captured by the reflected-light imaging unit 36. The pixel positions with respect to the same object in the fluorescence image and the reflected-excitation-light image of the observed region S coincide with each other. Every time the fluorescence imaging unit 37 captures the fluorescence image of the observed region S, the fluorescence imaging unit 37 transmits an image signal including the image information thus obtained to the image processing apparatus 4 sequentially.

The image processing apparatus 4 processes the image information of the observed region S captured by the reflected-light imaging unit 36 or the fluorescence imaging unit 37 to generate an output image to be displayed on the image display device 5. Specifically, the image processing apparatus 4 includes a reflected-light image storage unit 41 that stores therein the image information captured by the reflected-light imaging unit 36, a fluorescence image storage unit 42 that stores therein the image information captured by the fluorescence imaging unit 37, a motion vector calculator 43 that calculates motion vector information between the fluorescence image and the reflected-light image of the observed region S, an alignment processing unit 44 that performs alignment process on the fluorescence image and the reflected-light image of the observed region S based on the motion vector information, and an output image generating unit 45 that generates the output image to be displayed on the image display device 5.

The reflected-light image storage unit 41 stores therein the image information captured by the reflected-light imaging unit 36 based on the control of the filter controller 26 of the light source device 2. Specifically, the reflected-light image storage unit 41 acquires the filter information transmitted by the filter controller 26, and recognizes whether the filter of the rotating filter 24 actually positioned in the optical path in the light source device 2 is the white-light filter 24a or the excitation-light filter 24b based on the filter information thus acquired. If the filter positioned in the optical path in the light source device 2 is the white-light filter 24a, the reflected-light image storage unit 41 acquires the image information of the white-light image of the observed region S from the reflected-light imaging unit 36. If the filter positioned in the optical path in the light source device 2 is the excitation-light filter 24b, the reflected-light image storage unit 41 acquires the image information of the reflected-excitation-light image of the observed region S from the reflected-light imaging unit 36. The reflected-light image storage unit 41 performs synchronization process on pieces of the image information of the observed region S acquired from the reflected-light imaging unit 36 such that each pixel has color image information of three colors R, G, and B, and stores therein the pieces of the image information of the white-light image and the reflected-excitation-light image thus synchronized sequentially.

The fluorescence image storage unit 42 stores therein the image information captured by the fluorescence imaging unit 37 based on the control of the filter controller 26 of the light source device 2. Specifically, the fluorescence image storage unit 42 acquires the filter information transmitted by the filter controller 26, and recognizes whether the filter of the rotating filter 24 actually positioned in the optical path in the light source device 2 is the white-light filter 24a or the excitation-light filter 24b based on the filter information thus acquired. If the filter positioned in the optical path in the light source device 2 is the excitation-light filter 24b, the fluorescence image storage unit 42 acquires the image information of the fluorescence image of the observed region S from the fluorescence imaging unit 37, and stores therein the image information thus acquired sequentially. Note that, if the filter positioned in the optical path in the light source device 2 is the white-light filter 24a, the fluorescence image storage unit 42 acquires no image information from the fluorescence imaging unit 37.

Figure 6:
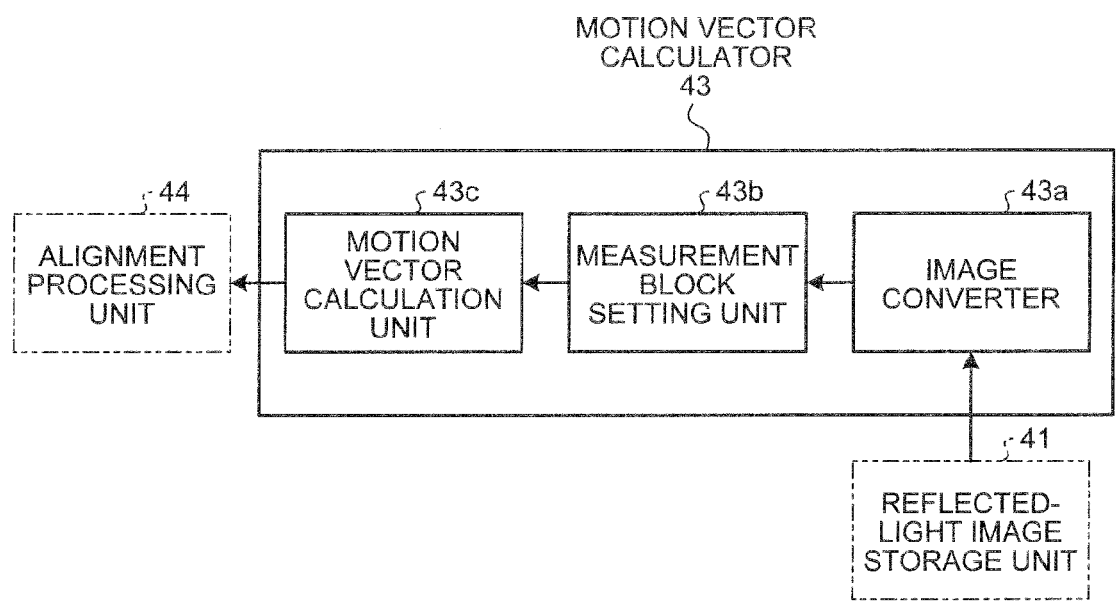
FIG. 6 is a block diagram schematically illustrating an exemplary configuration of a motion vector calculator of an image processing apparatus according to the first embodiment of the present invention.

The motion vector calculator 43 calculates motion vector information between the reflected-light image of the observed region S captured by the reflected-light imaging unit 36, and the fluorescence image of the observed region S captured by the fluorescence imaging unit 37. FIG. 6 is a block diagram schematically illustrating an exemplary configuration of the motion vector calculator of the image processing apparatus according to the first embodiment of the present invention. As illustrated in FIG. 6, the motion vector calculator 43 includes an image converter 43a that generates a motion vector calculation image, a measurement block setting unit 43b that sets motion vector measurement blocks on an image to be processed, and a motion vector calculation unit 43c that calculates motion vector information.

The image converter 43a converts the image information of the observed region S into a motion vector calculation image. Specifically, the image converter 43a reads the image information of the white-light image of the observed region S from the reflected-light image storage unit 41. The image converter 43a performs predetermined image conversion process on the image information of the white-light image thus acquired to generate a reference image that is one of the motion vector calculation images. Furthermore, the image converter 43a reads the image information of the reflected-excitation-light image of the observed region S from the reflected-light image storage unit 41. The image converter 43a performs predetermined image conversion process on the image information of the reflected excitation light thus acquired to generate a target image that is one of the motion vector calculation images. The image converter 43a transmits the motion vector calculation image (reference image) corresponding to the white-light image, and the motion vector calculation image (target image) corresponding to the reflected-excitation-light image to the measurement block setting unit 43b.

The measurement block setting unit 43b sets motion vector measurement blocks on the image to be processed. Specifically, the measurement block setting unit 43b acquires the reference image serving as one of the motion vector calculation images from the image converter 43a, and sets a predetermined number of motion vector measurement blocks on the reference image thus acquired. Furthermore, the measurement block setting unit 43b acquires the target image serving as the other of the motion vector calculation images from the image converter 43a, and sets a predetermined number of pixel blocks to be used for matching process with the measurement blocks on the reference image described above on the target image thus acquired. The measurement block setting unit 43b transmits each of the motion vector calculation images (reference image and target image) thus processed to the motion vector calculation unit 43c.

The motion vector calculation unit 43c calculates the motion vector information between the fluorescence image and the reflected-light image of the observed region S. Specifically, the motion vector calculation unit 43c acquires the reference image and the target image serving as each of the motion vector calculation images thus processed from the measurement block setting unit 43b. The motion vector calculation unit 43c uses a known method, such as a block matching method, for detecting each pixel block on the target image highly correlated with each measurement block on the reference image to calculate the motion vector information between the reference image and the target image. The reference image used herein corresponds to the white-light image of the observed region S captured by the reflected-light imaging unit 36. By contrast, the target image used herein corresponds to the reflected-excitation-light image of the observed region captured by the reflected-light imaging unit 36 at the same imaging timing as that of the fluorescence image of the observed region S captured by the fluorescence imaging unit 37. In other words, the pixel positions with respect to the same object in the target image and the fluorescence image of the observed region S coincide with each other. The motion vector calculation unit 43c calculates the motion vector information between the target image corresponding to the reflected-excitation-light image at the same imaging timing as that of the fluorescence image, and the reference image corresponding to the white-light image as the motion vector information between the fluorescence image and the white-light image of the observed region S. The motion vector calculation unit 43c transmits the calculation result of the motion vector information thus calculated to the alignment processing unit 44.

The alignment processing unit 44 performs alignment process on the fluorescence image and the reflected-light image of the observed region S to correct misalignment of the object between the fluorescence image and the reflected-light image. Specifically, the alignment processing unit 44 reads the image information of the white-light image of the observed region S captured by the reflected-light imaging unit 36 from the reflected-light image storage unit 41, and reads the image information of the fluorescence image of the observed region S captured by the fluorescence imaging unit 37 from the fluorescence image storage unit 42. Furthermore, the alignment processing unit 44 acquires the motion vector information calculated by the motion vector calculation unit 43c, that is, the motion vector information between the fluorescence image and the white-light image of the observed region S from the motion vector calculator 43. The alignment processing unit 44 performs the alignment process for aligning the pixel positions with respect to the same object (e.g., the lesion K) between the fluorescence image and the white-light image of the observed region S based on the motion vector information thus acquired. In this manner, the alignment processing unit 44 corrects the misalignment of the object between the fluorescence image and the reflected-light image. The alignment processing unit 44 transmits the pieces of the image information of the fluorescence image and the white-light image thus aligned with each other to the output image generating unit 45.

If the numbers of pixels are different in the reflected-light imaging unit 36 and the fluorescence imaging unit 37, the alignment processing unit 44 performs enlargement process or reduction process on the fluorescence image captured by the fluorescence imaging unit 37 to cause the numbers of pixels in the white-light image captured by the reflected-light imaging unit 36 and the fluorescence image captured by the fluorescence imaging unit 37 to coincide with each other. The alignment processing unit 44 performs the alignment process described above on the fluorescence image and the white-light image of which numbers of pixels are caused to coincide with each other.

The output image generating unit 45 generates an output image to be displayed on the image display device 5 based on the pieces of the image information aligned with each other by the alignment processing unit 44. Specifically, the output image generating unit 45 acquires the pieces of the image information of the fluorescence image and the white-light image of the observed region S thus aligned with each other from the alignment processing unit 44. The output image generating unit 45 normalizes the brightness of the fluorescence image based on the brightness of the white-light image thus acquired to generate a normalized fluorescence image of the observed region S. In this case, the output image generating unit 45 generates a normalization image serving as a brightness signal image of the white-light image acquired from the alignment processing unit 44. The output image generating unit 45 divides the brightness value of the fluorescence image on which the alignment process is performed by the brightness value of the normalization image thus generated, that is, by the brightness value of the white-light image of the observed region S on which the alignment process described above is performed. In this manner, the output image generating unit 45 normalizes the brightness value of each pixel of the fluorescence image of the observed region S. As a result, the output image generating unit 45 generates the normalized fluorescence image of the observed region S. The normalized fluorescence image of the observed region S is a fluorescence image in which the intensity of the fluorescence that changes depending on the distance from the observed region S serving as the object to the fluorescence imaging unit 37 is corrected. Therefore, in the normalized fluorescence image of the observed region S, the lesion K serving as a source generating the fluorescence by the irradiation of the excitation light is depicted with pixels having relatively high brightness regardless of the distance from the observed region S to the fluorescence imaging unit 37. The output image generating unit 45 transmits the normalized fluorescence image of the observed region S thus generated, and the white-light image of the observed region S to the image display device 5 to cause the image display device 5 to display the normalized fluorescence image and the white-light image of the observed region S. In this case, the output image generating unit 45 may transmit the normalized fluorescence image and the white-light image of the observed region S to the image display device 5 as different pieces of output image information, or may transmit the normalized fluorescence image and the white-light image of the observed region S to the image display device 5 as output image information obtained by superimposing the images.

The image display device 5 displays the image information processed by the image processing apparatus 4. Specifically, the image display device 5 is realized by using a desired display, such as a CRT display and a liquid-crystal display. The image display device 5 acquires the image information of the observed region S from the output image generating unit 45 of the image processing apparatus 4, and displays at least the normalized fluorescence image of the observed region S based on the image information thus acquired. In this case, the image display device 5 may display the white-light image and the normalized fluorescence image of the observed region S acquired from the output image generating unit 45 in a manner arranged side by side, or may display the normalized fluorescence image of the observed region S in a manner superimposed on the white-light image of the observed region S.

Figure 7:
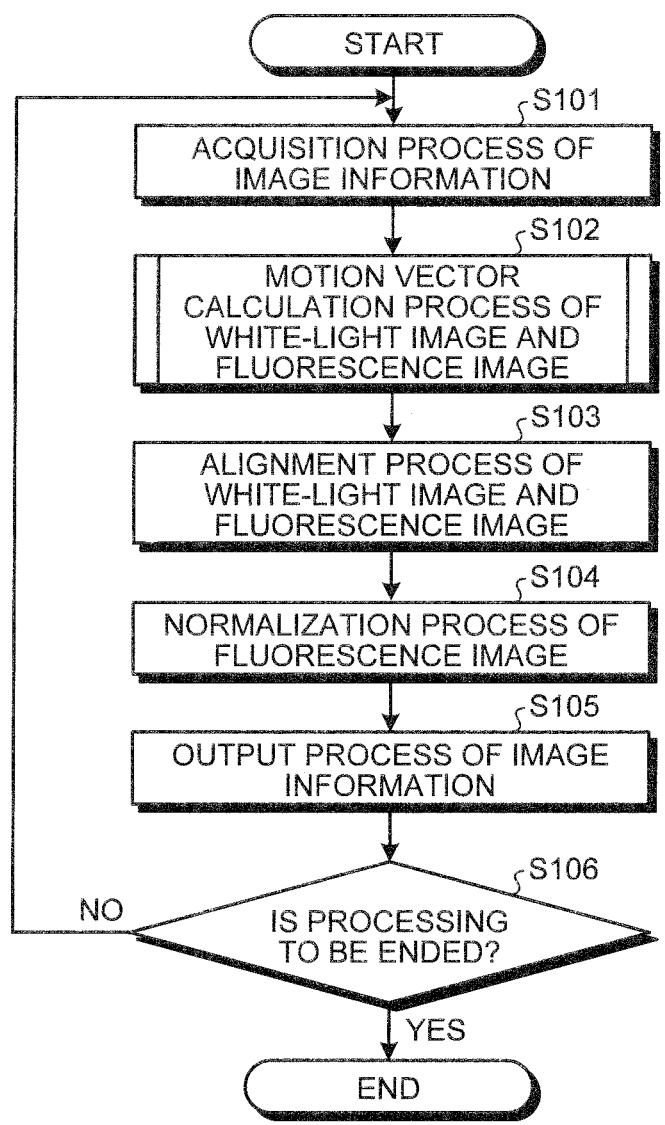
FIG. 7 is a flowchart exemplifying processing of the image processing apparatus according to the first embodiment of the present invention.

Operations performed by the image processing apparatus 4 according to the first embodiment of the present invention will now be described. FIG. 7 is a flowchart exemplifying processing of the image processing apparatus according to the first embodiment of the present invention. The image processing apparatus 4 according to the first embodiment performs the processing illustrated in FIG. 7 to cause the image display device 5 to display the image information of the observed region S.

Specifically, as illustrated in FIG. 7, the image processing apparatus 4 acquires the image information of the observed region S (Step S101). At Step S101, the reflected-light image storage unit 41 acquires the white-light image of the observed region S captured by the reflected-light imaging unit 36 at a timing when the white-light filter 24a of the rotating filter 24 is positioned in the optical path, that is, at a timing when the observed region S is irradiated with the white light, and stores therein the white-light image thus acquired as color image information. Note that, at the timing when the observed region S is irradiated with the white light, the fluorescence image storage unit 42 acquires no image information. By contrast, the fluorescence image storage unit 42 acquires the fluorescence image of the observed region S captured by the fluorescence imaging unit 37 at a timing when the excitation-light filter 24b of the rotating filter 24 is positioned in the optical path, that is, at a timing when the observed region S is irradiated with the excitation light, and stores therein the fluorescence image thus acquired as monochrome image information. At the timing when the observed region S is irradiated with the excitation light, the reflected-light image storage unit 41 acquires the reflected-excitation-light image of the observed region S captured by the reflected light imaging unit 36, and stores therein the reflected-excitation-light image thus acquired as color image information.

Subsequently, the image processing apparatus 4 calculates the motion vector information between the white-light image and the fluorescence image of the observed region S acquired at Step S101 (Step S102). At Step S102, the motion vector calculator 43 reads the pieces of the image information of the white-light image and the reflected-excitation-light image of the observed region S from the reflected-light image storage unit 41. The motion vector calculator 43 calculates the motion vector information between the white-light image and the reflected-excitation-light image of the observed region thus read as the motion vector information between the fluorescence image and the white-light image of the observed region S acquired at Step S101.

The image processing apparatus 4 then performs the alignment process on the white-light image and the fluorescence image of the observed region S at Step S101 (Step S103). At Step S103, the alignment processing unit 44 acquires the white-light image of the observed region S at Step S101 from the reflected-light image storage unit 41, and acquires the fluorescence image of the observed region S at Step S101 from the fluorescence image storage unit 42. Furthermore, the alignment processing unit 44 acquires the motion vector information calculated by the motion vector calculation unit 43c at Step S102. The alignment processing unit 44 performs the alignment process for aligning the pixel positions with respect to the same object in the fluorescence image and the white-light image of the observed region S based on the motion vector information thus acquired. In this manner, the alignment processing unit 44 corrects the misalignment of the object between the fluorescence image and the white-light image (e.g., misalignment of the lesion K between both of the images).

Subsequently, the image processing apparatus 4 performs the normalization process on the fluorescence image of the observed region S on which the alignment process is performed at Step S103 (Step S104). At Step S104, the output image generating unit 45 acquires the fluorescence image and the white-light image of the observed region S aligned with each other at Step S103 from the alignment processing unit 44. The output image generating unit 45 calculates the brightness signal of the white-light image thus acquired, and generates the normalization image serving as the brightness signal image of the white-light image based on the brightness signal thus calculated. The output image generating unit 45 then divides the brightness value of the fluorescence image on which the alignment process is performed by the brightness value of the normalization image thus generated, thereby normalizing the brightness value of each pixel of the fluorescence image. In this manner, the output image generating unit 45 achieves the normalization process of the fluorescence image of the observed region S.

The image processing apparatus 4 then performs output process of the image information of the observed region S to be displayed on the image display device 5 (Step S105). At Step S105, the output image generating unit 45 generates a normalized fluorescence image of the observed region S based on the normalization process of the fluorescence image at Step S104. The output image generating unit 45 transmits the image information of the normalized fluorescence image of the observed region S to the image display device 5 as the output image information of the observed region S to be displayed on the image display device 5. As a result, the image display device 5 displays the normalized fluorescence image of the observed region S.

The normalized fluorescence image of the observed region S is a fluorescence image in which differences in the intensity of the fluorescence caused by differences in the distance from the observed region S serving as the object to the fluorescence imaging unit 37 is corrected. The image display device 5 displays the lesion K in the observed region S with pixels having relatively high brightness regardless of the distance from the observed region S to the fluorescence imaging unit 37 in the normalized fluorescence image of the observed region S.

At Step S105, the output image generating unit 45 may transmit the image information of the white-light image of the observed region S to the image display device 5 together with the image information of the normalized fluorescence image of the observed region S as the output image information of the observed region S to be displayed on the image display device 5. This allows the image display device 5 to display the normalized fluorescence image and the white-light image of the observed region S in a manner arranged side by side.

Furthermore, at Step S105, the output image generating unit 45 may transmit the image information obtained by superimposing the normalized fluorescence image and the white-light image of the observed region S to the image display device 5 as the output image information of the observed region S to be displayed on the image display device 5. In this case, correspondingly to a pixel of the object-of-interest such as the lesion K in the normalized fluorescence image, the output image generating unit 45 performs desired color conversion process on the signal value of a pixel of the same object-of-interest (e.g., the lesion K) in the white-light image, thereby superimposing the image information of the normalized fluorescence image on the white-light image. Furthermore, the output image generating unit 45 performs arbitrary post-process, such as gamma conversion process, edge enhancement process, enlargement process, and reduction process, on the superimposed image information of the white-light image and the normalized fluorescence image, and transmits the superimposed image information on which the post-process is performed to the image display device 5.

The output image generating unit 45 may perform arbitrary color conversion process uniformly on the entire white-light image of the observed region S regardless of the position on the image, and superimpose the information of the normalized fluorescence image on the white-light image on which the color conversion process is performed. Alternatively, instead of the normalized fluorescence image of the observed region S, the output image generating unit 45 may superimpose the fluorescence image of the observed region S on which the alignment process is performed (that is, the fluorescence image prior to the normalization process) and the white-light image of the observed region S.

After the completion of the processing at Step S105, if the operating unit (not illustrated) performs processing end operation such as an OFF operation (YES at Step S106), the image processing apparatus 4 ends the processing. By contrast, the processing end operation is not performed yet (NO at Step S106), the image processing apparatus 4 returns to Step S101, and repeats the processing subsequent to Step S101.

Figure 8:
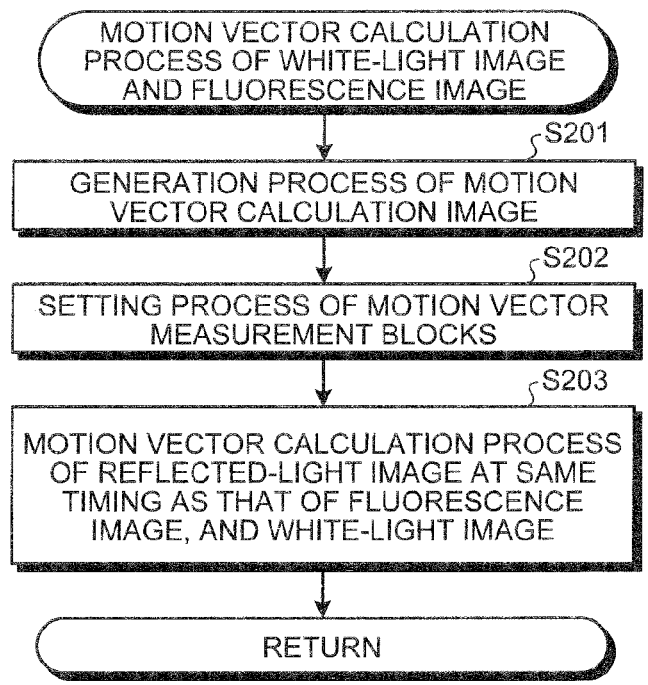
FIG. 8 is a flowchart exemplifying processing of motion vector calculation process of a white-light image and a fluorescence image of an observed region in the first embodiment.
Figure 9:
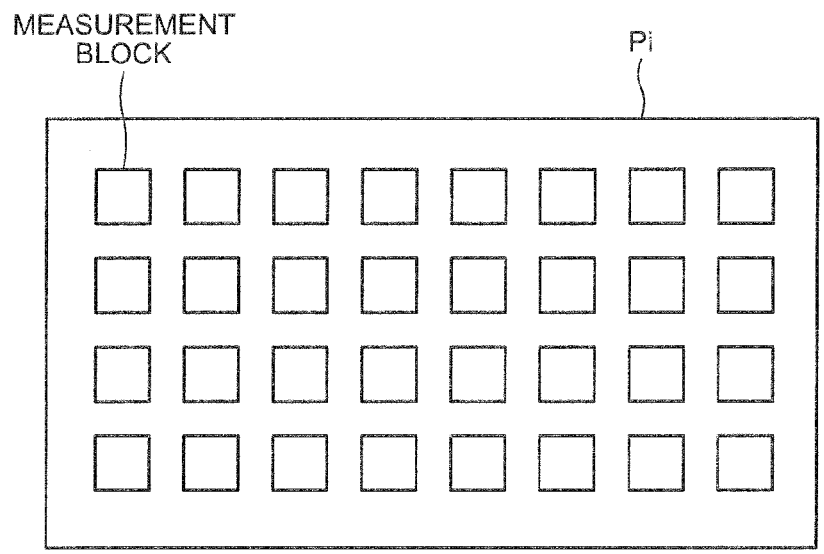
FIG. 9 is a schematic exemplifying a state in which motion vector measurement blocks are set on a motion vector calculation image.
Figure 10:
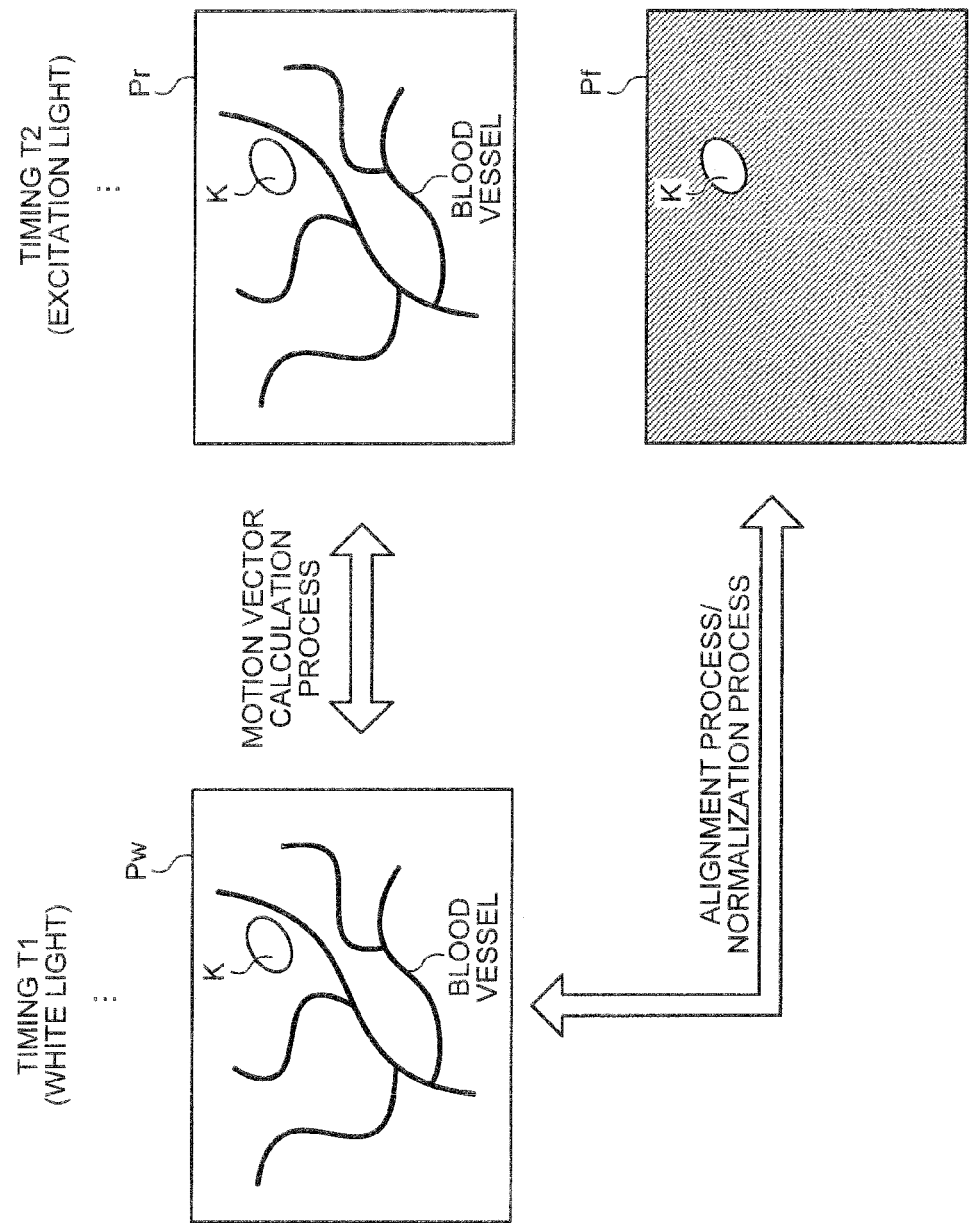
FIG. 10 is a schematic for specifically explaining the motion vector calculation process of the white-light image and the fluorescence image of the observed region in the first embodiment.

A detailed description will be made of the motion vector calculation process of the white-light image and the fluorescence image of the observed region S performed by the motion vector calculator 43 of the image processing apparatus 4 at Step S102. FIG. 8 is a flowchart exemplifying processing of the motion vector calculation process of the white-light image and the fluorescence image of the observed region in the first embodiment. FIG. 9 is a schematic exemplifying a state in which motion vector measurement blocks are set on a motion vector calculation image. FIG. 10 is a schematic for specifically explaining the motion vector calculation process of the white-light image and the fluorescence image of the observed region in the first embodiment.

When performing the motion vector calculation process of the white-light image and the fluorescence image of the observed region S at Step S102, the motion vector calculator 43, as illustrated in FIG. 8, generates a motion vector calculation image (Step S201). At Step S201, the image converter 43a acquires the white-light image of the observed region S at Step S101 from the reflected-light image storage unit 41. The image converter 43a calculates the brightness signal of the white-light image thus acquired, and performs gain adjustment process for making the brightness uniform on the brightness signal thus calculated to generate the brightness signal image corresponding to the white-light image, that is, a reference image serving as one of the motion vector calculation images. Furthermore, the image converter 43a acquires the reflected-excitation-light image of the observed region S at Step S101 from the reflected-light image storage unit 41. The image converter 43a calculates the brightness signal of the reflected-excitation-light image thus acquired, and performs gain adjustment process for making the brightness uniform on the brightness signal thus calculated to generate the brightness signal image corresponding to the reflected-excitation-light image, that is, a target image serving as one of the motion vector calculation images.

A brightness signal Y for generating the motion vector calculation image is calculated using a pixel value R of a red component, a pixel value G of a green component, and a pixel value B of a blue component of the white-light image or the reflected-excitation-light image of the observed region S by Equation: Brightness Signal $Y=0.29 \times R+0.6 \times G+0.11 \times B$. The image converter 43a, instead of calculating the brightness signal Y, may extract the pixel value of an R channel including many wavelength bands of the excitation light from the white-light image or the reflected-excitation-light image of the observed region S alone, and perform the gain adjustment process on the pixel value of the R channel thus extracted to generate the motion vector calculation images (reference image and target image).

The motion vector calculator 43 then sets the motion vector measurement blocks on the motion vector calculation image generated at Step S201 (Step S202). At Step S202, the measurement block setting unit 43b acquires a reference image Pi serving as one of the motion vector calculation images at Step S201 from the image converter 43a, and sets a predetermined number of motion vector measurement blocks on the reference image Pi thus acquired. In this case, as illustrated in FIG. 9, for example, the measurement block setting unit 43b sets the motion vector measurement blocks of 32 blocks on the reference image Pi in a grid-like pattern. Note that the setting state of the motion vector measurement blocks on the reference image Pi illustrated in FIG. 9 is an example, and the measurement block setting unit 43b may set a desired number of motion vector measurement blocks on the reference image Pi in a desired pattern. By contrast, the measurement block setting unit 43b acquires a target image Pj serving as the other of the motion vector calculation images at Step S201 from the image converter 43a. The measurement block setting unit 43b sets a predetermined number of pixel blocks to be used for matching process with the measurement blocks on the reference image Pi described above on the target image Pj thus acquired.

Subsequently, the motion vector calculator 43 calculates the motion vector information between the reflected-light image at the same timing as that of the fluorescence image of the observed region S at Step S101, and the white-light image of the observed region S at Step S101 (Step S203).

At Step S203, the motion vector calculation unit 43c acquires the reference image Pi and the target image Pj serving as the motion vector calculation images at Step S202 from the measurement block setting unit 43b. The motion vector calculation unit 43c uses a known method, such as a block matching method, to detect a pixel block on the target image Pj highly correlated with an arbitrary measurement block on the reference image Pi. The motion vector calculation unit 43c then calculates vector information indicating relative misalignment between the measurement block on the reference image Pi and the pixel block on the target image Pj highly correlated with each other as the motion vector information between the reference image Pi and the target image Pj. The motion vector calculation unit 43c calculates the motion vector information for all of the measurement blocks on the reference image Pi, and performs averaging process of the motion vector information based on all the pieces of the motion vector information thus obtained to calculate representative motion vector information between the reference image Pi and the target image Pj. The motion vector calculation unit 43c outputs the representative motion vector information thus calculated as the motion vector information between the fluorescence image and the white-light image of the observed region S.

Specifically, as illustrated in FIG. 10, a white-light image Pw of the observed region S corresponding to the reference image Pi is a reflected-light image captured by the reflected-light imaging unit 36 at a timing T1 when the observed region S is irradiated with the white light. By contrast, a reflected-excitation-light image Pr of the observed region S corresponding to the target image Pj is a reflected-light image captured by the reflected-light imaging unit 36 at a timing 12 when the observed region S is irradiated with the excitation light. At the timing T2, the fluorescence imaging unit 37 captures a fluorescence image Pf of the observed region S. In other words, the reflected-excitation-light image Pr and the fluorescence image Pf of the observed region S are images captured at the same timing, and the pixel positions with respect to the same object (e.g., the lesion K) in the target image Pj based on the reflected-excitation-light image Pr and the fluorescence image Pf coincide with each other. The motion vector calculation unit 43c calculates the motion vector information between the reference image Pi corresponding to the white-light image Pw at the timing T1, and the target image Pj corresponding to the reflected-excitation-light image Pr at the timing T2. In this manner, the motion vector calculation unit 43c calculates the motion vector information between the fluorescence image Pf at the same timing as that of the reflected-excitation-light image Pr, and the white-light image Pw.

The white-light image Pw of the observed region S is a color image depicting the observed region S, and includes shape information, such as a blood vessel structure, in the observed region S. By contrast, the fluorescence image Pf of the observed region S is an image depicting the lesion K from which the fluorescence is generated by the irradiation of the excitation light, and includes no shape information, such as a blood vessel structure, in the observed region S. Therefore, it is difficult to calculate the motion vector information between the white-light image Pw and the fluorescence image Pf directly. By contrast, the motion vector calculation unit 43c calculates the motion vector information between the reflected-excitation-light image Pr that is a reflected-light image whose pixel positions with respect to the same object coincide with those of the fluorescence image Pf, and that includes the shape information, such as a blood vessel structure, in the observed region S, and the white-light image Pw. This allows the motion vector calculator 43 to calculate the motion vector information between the white-light image Pw and the fluorescence image Pf indirectly.

The methods for detecting pixel blocks highly correlated with each other based on the block matching method performed by the motion vector calculator 43 include, for example, a method in which Sum of Squared Difference (SSD), Sum of Absolute Difference (SAD), or the like is used. This is a method for calculating a pixel block area I on the target image Pj highly correlated with a measurement block area I on the reference image Pi. The Sum of Squared Difference (SSD), and the Sum of Absolute Difference (SAD) are expressed by Equations (1) and (2) using a pixel level Lp of a pixel position p in the measurement block area I, and a pixel level Lq of a pixel position q in the measurement block area I', respectively, and the correlativity is estimated to be higher as the values are smaller.

$$SSD(I, I') = \sum_{p \in I, q \in I'} (Lp - Lq)^2 \qquad (1)$$

$$SAD(I, I') = \sum_{p \in I, q \in I'} \|Lp - Lq\| \qquad (2)$$

After the completion of the processing at Step S203, the motion vector calculator 43 returns to Step S102 illustrated in FIG. 7. Subsequently, the image processing apparatus 4 goes to Step S103 as described above, and performs the processing subsequent to Step S103.

Figure 11:
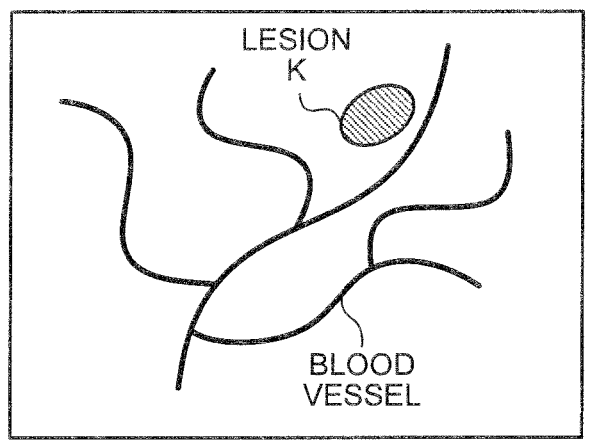
FIG. 11 is a schematic illustrating a specific example of an image obtained by superimposing the white-light, image and the fluorescence image of the observed region.

In the white-light image Pw and the fluorescence image Pf for which the motion vector information is specified, the misalignment with respect to the same object such as the lesion K is corrected by the alignment process at Step S103. Furthermore, the brightness of the fluorescence image Pf aligned with the white-light image Pw is normalized with high accuracy at Step S104, thereby correcting the intensity of the fluorescence in the fluorescence image Pf caused by differences in the distance from the observed region S serving as the object to the fluorescence imaging unit 37 precisely. As a result, without being affected by the misalignment of the object between both of the images, the output image generating unit 45 can generate the fluorescence image Pf depicting the lesion K having relatively high brightness regardless of the distance from the observed region S to the fluorescence imaging unit 37, that is, the normalized fluorescence image of the observed region S accurately. Furthermore, by superimposing the fluorescence image Pf on which the alignment process is performed or the normalized fluorescence image, and the white-light image Pw as described above, the output image generating unit 45 can generate a color image of the observed region S capable of emphasizing the lesion K while displaying the blood vessel structure of the observed region S as illustrated in FIG. 11, and display the color image thus generated on the image display device 5.

As described above, in the first embodiment of the present invention, the fluorescence image based on the fluorescence generated from the observed region by the irradiation of the excitation light, and the reflected-excitation-light image based on the excitation light reflected from the observed region are captured. The motion vector information between the white-light image captured by irradiating the observed region with the white light and the reflected-excitation-light image is calculated. The misalignment of the object between the fluorescence image and the white-light image of the observed region is corrected based on the motion vector information thus calculated. The fluorescence image is divided by the white-light image thus corrected, thereby normalizing the brightness of the fluorescence image. Therefore, the normalization process of the fluorescence image can be performed without being affected by the misalignment of the object between the normalization image generated based on the white-light image and the fluorescence image to be normalized. Thus, the accuracy in the normalization process of the fluorescence image is improved, thereby making it possible to correct the brightness of the fluorescence image of the observed region precisely. As a result, it is possible to depict an abnormal tissue such as a lesion in the observed region with pixels having relatively high brightness in the fluorescence image regardless of the distance from the object to the imaging unit, and to improve detectability of the abnormal tissue in the subject with the fluorescence image of the observed region.

Furthermore, in the first embodiment, the motion vector information between the fluorescence image and the white-light image of the observed region can be calculated indirectly by using the reflected-excitation-light image at the same imaging timing as that of the fluorescence image that includes little shape information. Based on the motion vector information thus calculated, the misalignment of the object between the fluorescence image and the white-light image of the observed region can be corrected with high accuracy. Therefore, the abnormal tissue such as a lesion depicted in the fluorescence image, and the same abnormal tissue depicted in the white-light image can be superimposed with high accuracy. As a result, it is possible to display the in-vivo state of the observed region such as a blood, vessel structure in color, and to emphasize the abnormal tissue such as a lesion accurately.

Second Embodiment

A second embodiment of the present invention will now be described. In the first embodiment, to calculate the motion vector information between the fluorescence image of the observed region S and the reflected-light image of the observed region S, the motion vector information between the reflected-excitation-light image of the observed region S captured at the same timing as that of the fluorescence image, and the white-light image of the observed region S is calculated. However, in the second embodiment, to calculate the motion vector information between the fluorescence image of the observed region S and the reflected-light image of the observed region S, motion vector information between two white-light images of the observed region S that are sequential in chronological order with the fluorescence image interposed therebetween.

Figure 12:
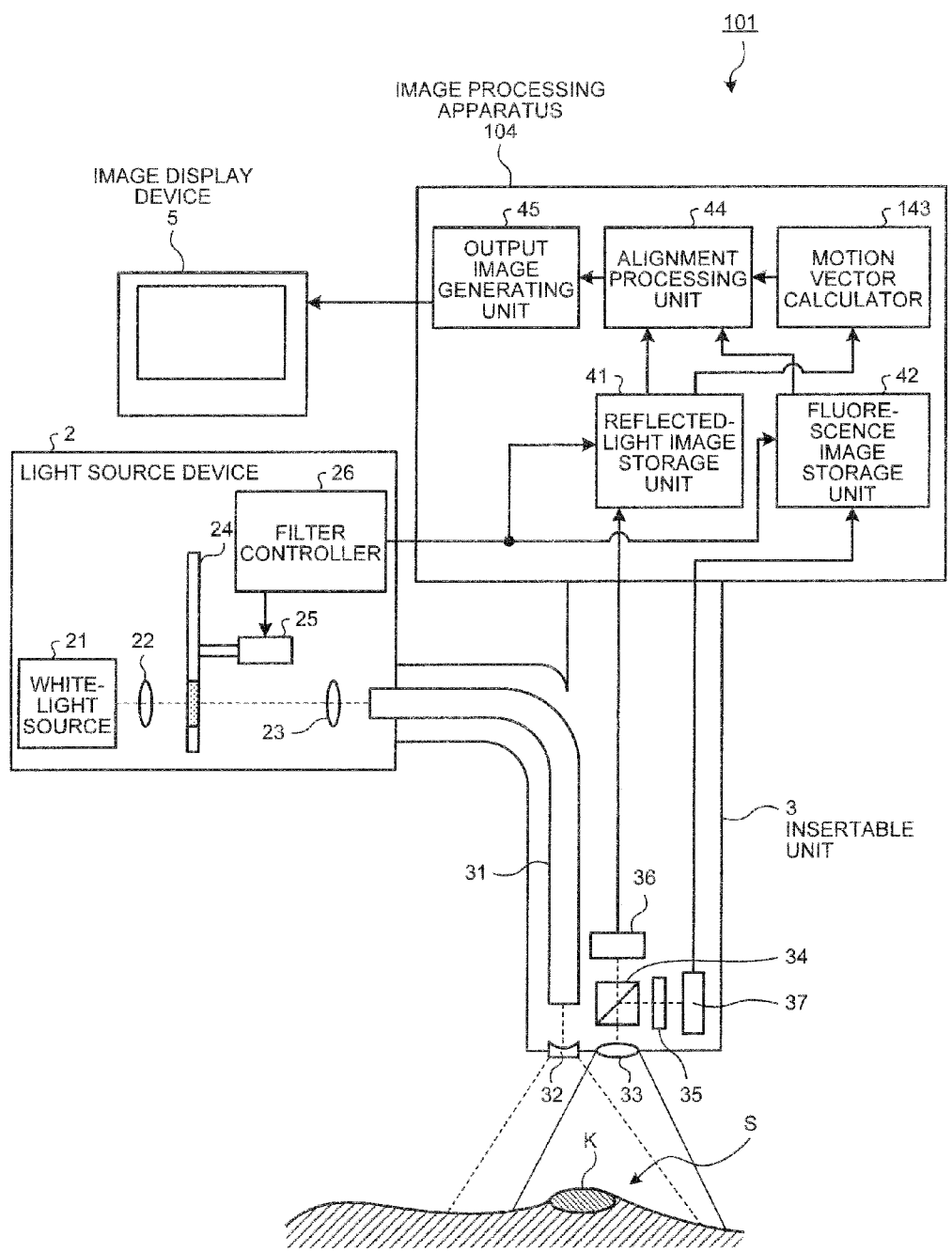
FIG. 12 is a block diagram schematically illustrating an exemplary configuration of an endoscope apparatus according to a second embodiment of the present invention.

FIG. 12 is a block diagram schematically illustrating an exemplary configuration of an endoscope apparatus according to the second embodiment of the present invention. As illustrated in FIG. 12, an endoscope apparatus 101 according to the second embodiment includes an image processing apparatus 104 instead of the image processing apparatus 4 of the endoscope apparatus 1 according to the first embodiment. The image processing apparatus 104 according to the second embodiment includes a motion vector calculator 143 instead of the motion vector calculator 43 of the image processing apparatus 4 according to the first embodiment. In the second embodiment, the reflected-light imaging unit 36, at Step S101 illustrated in FIG. 7, captures the white-light image and the reflected-excitation-light image of the observed region S alternately at time intervals specified in advance for the filter controller 26, and captures the white-light images of two frames that are sequential in chronological order with the fluorescence image of one frame interposed therebetween for one observed region S. By contrast, the fluorescence imaging unit 37 captures the fluorescence image of the observed region S at the same imaging timing as that of the reflected-excitation-light image captured by the reflected-light imaging unit 36. In other word, the fluorescence image and the white-light image of the observed region are captured alternately at the time intervals specified in advance. Other components are the same as those of the first embodiment, and the same reference numerals are assigned to the same components.

The image processing apparatus 104 includes the reflected-light image storage unit 41, the fluorescence image storage unit 42, the alignment processing unit 44, and the output image generating unit 45, and further includes the motion vector calculator 143 instead of the motion vector calculator 43 of the image processing apparatus 4 according to the first embodiment. In the image processing apparatus 104, the reflected-light image storage unit 41 stores therein the reflected-excitation-light image and the white-light image of the observed region S captured consecutively in chronological order by the reflected-light imaging unit 36 sequentially. Specifically, the reflected-light image storage unit 41 stores therein the reflected-excitation-light image of one frame, and the white-light images of two frames that are sequential in chronological order with the reflected-excitation-light image interposed therebetween as color image information sequentially for one observed region S. Note that the image processing apparatus 104 has the same functions as those of the image processing apparatus 4 according to the first embodiment other than the functions of the reflected-light image storage unit 41 and the motion vector calculator 143.

Figure 13:
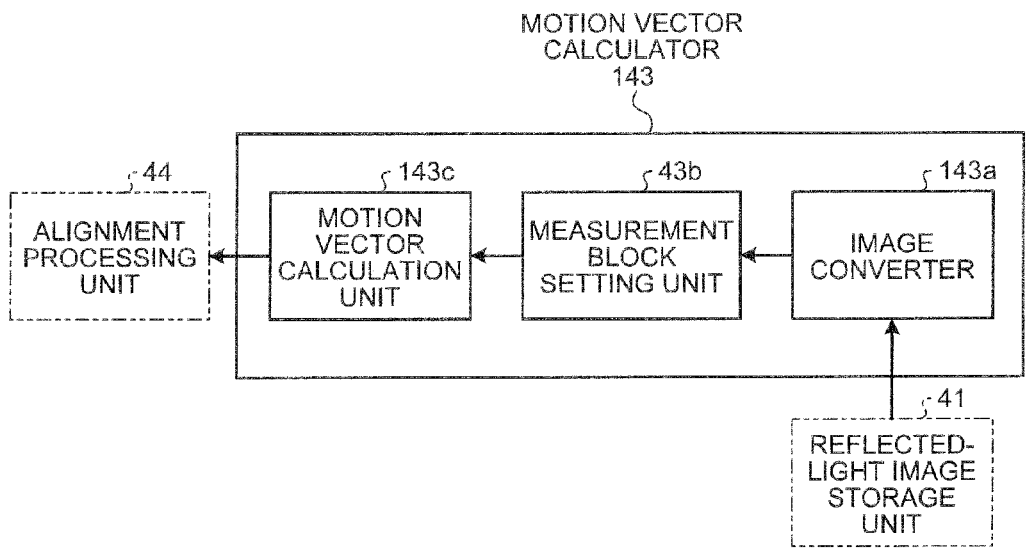
FIG. 13 is a block diagram schematically illustrating an exemplary configuration of a motion vector calculator of an image processing apparatus according to the second embodiment of the present invention.

The motion vector calculator 143 calculates the motion vector information between two reflected-light images of the observed region S that are sequential in chronological order with the fluorescence image of the observed region S interposed therebetween. Based on the motion vector information thus calculated, and the imaging time interval of the fluorescence image and the reflected-light image of the observed region S, the motion vector calculator 143 calculates the motion vector information between the fluorescence image and the reflected-light image of the observed region S. FIG. 13 is a block diagram schematically illustrating an exemplary configuration of the motion vector calculator of the image processing apparatus according to the second embodiment of the present invention. As illustrated in FIG. 13, the motion vector calculator 143 according to the second embodiment includes the measurement block setting unit 43b, and further includes an image converter 143a instead of the image converter 43a, and a motion vector calculation unit 143c instead of the motion vector calculation unit 43c of the motion vector calculator 43 in the first embodiment.

The image converter 143a converts the image information of the observed region S into the motion vector calculation image. Specifically, the image converter 143a reads the reflected-excitation-light image of the observed region S, and the white-light images of two frames that are sequential with the reflected-excitation-light image interposed therebetween sequentially in chronological order from the reflected-light image storage unit 41. The image converter 143a performs the same image conversion process as that in the image converter 43a in the first embodiment on the image information of the white-light image of the observed region S thus read first, and generates a reference image that is one of the motion vector calculation images. Furthermore, the image converter 143a performs the same image conversion process as that in the image converter 43a in the first embodiment on the image information of the white-light image of the observed region S thus read subsequent to the reflected-excitation-light image, and generates a target image that is one of the motion vector calculation images. The image converter 143a transmits the motion vector calculation image (reference image) corresponding to the first white-light image, the motion vector calculation image (target image) corresponding to the next white-light image, and the reflected-excitation-light image between both of the motion vector calculation images to the measurement block setting unit 43b sequentially in chronological order.

The motion vector calculation unit 143c calculates the motion vector information between the fluorescence image and the reflected-light image of the observed region S. Specifically, the motion vector calculation unit 143c acquires the reference image and the target image serving as each of the motion vector calculation images thus processed, and the reflected-excitation-light image between both of the motion vector images from the measurement block setting unit 43b sequentially in chronological order. The motion vector calculation unit 143c uses a known method, such as the block matching method, for detecting each pixel block on the target image highly correlated with each measurement block on the reference image to calculate the motion vector information between the reference image and the target image. The reference image and the target image used herein correspond to the two white-light images of the observed region S captured sequentially with the reflected-excitation-light image of the observed region S interposed therebetween by the reflected-light imaging unit 36, respectively. By contrast, the reflected-excitation-light image is the reflected-light image of the observed region S captured by the reflected-light imaging unit 36 at the same imaging timing as that of the fluorescence image of the observed region S captured by the fluorescence imaging unit 37, and the pixel positions with respect to the same object in the reflected-excitation-light image and the fluorescence image coincide with each other. The motion vector calculation unit 143c calculates the motion vector information between the reference image and the target image, that is, the motion vector information between the two white-light images of the observed region S that are sequential in chronological order with the reflected-excitation-light image interposed therebetween. Based on the motion vector information thus calculated, and the imaging time intervals between the reflected-light images (specifically, the first white-light image, the reflected-excitation-light image, and the next white-light image) of the observed region S, the motion vector calculation unit 143c calculates the motion vector information between the first white-light image and the reflected-excitation-light image of the observed region S eventually. The motion vector calculation unit 143c transmits the final calculation result of the motion vector information thus calculated to the alignment processing unit 44 as the motion vector information between the fluorescence image and the white-light image of the observed region S.

Operations performed by the image processing apparatus 104 according to the second embodiment of the present invention will now be described. The image processing apparatus 104 according to the second embodiment operates in the same manner as the image processing apparatus 4 according to the first embodiment other than the motion vector calculation process of the white-light image and the fluorescence image of the observed region S. In other words, the image processing apparatus 104 performs the same processing as that in the image processing apparatus 4 according to the first embodiment in the processing from Step S101 to Step S106 illustrated in FIG. 7 other than Step S102.

Figure 14:
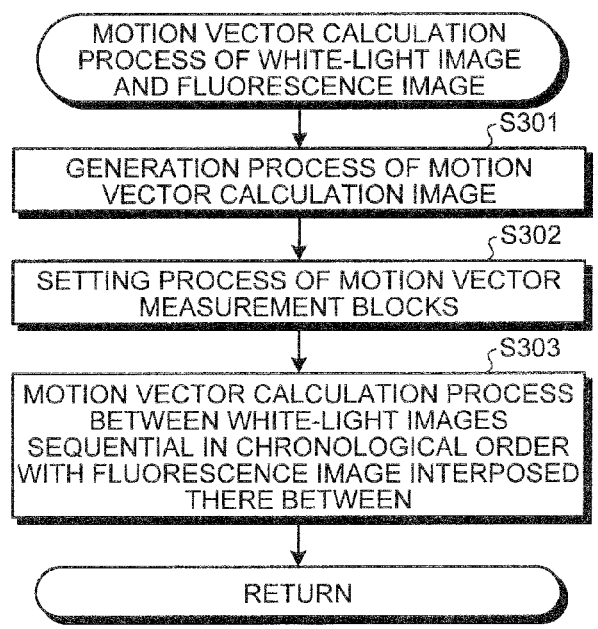
FIG. 14 is a flowchart exemplifying processing of motion vector calculation process of a white-light image and a fluorescence image of an observed region in the second embodiment.
Figure 15:
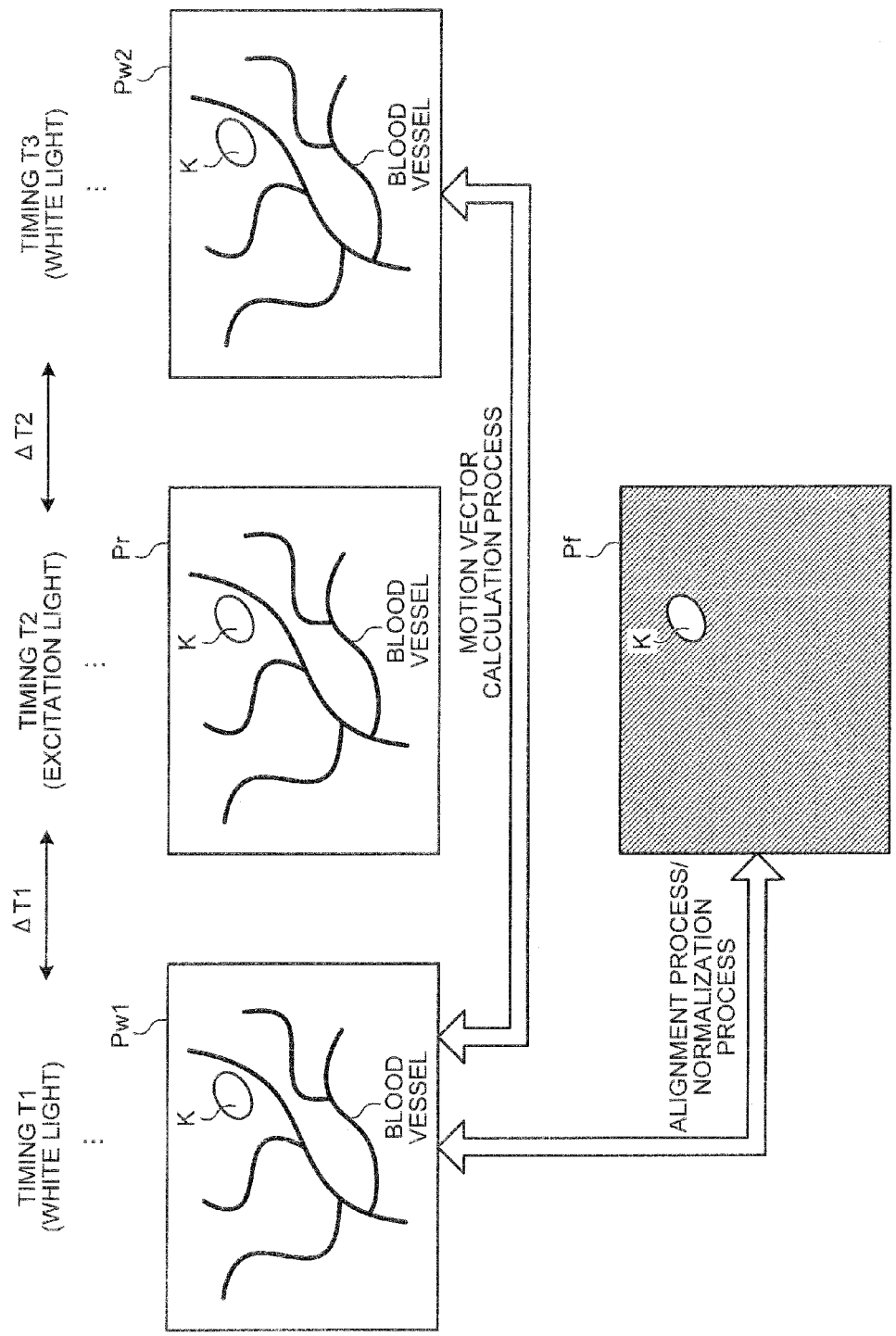
FIG. 15 is a schematic for specifically explaining the motion vector calculation process of the white-light image and the fluorescence image of the observed region in the second embodiment.

FIG. 14 is a flowchart exemplifying processing of the motion vector calculation process of the white-light image and the fluorescence image of the observed region in the second embodiment. FIG. 15 is a schematic for specifically explaining the motion vector calculation process of the white-light image and the fluorescence image of the observed region in the second embodiment.

When the age processing apparatus 104 performs the motion vector calculation process of the white-light image and the fluorescence image of the observed region S at Step S102, the motion vector calculator 143 of the image processing apparatus 104 firstly generates a motion vector calculation image as illustrated in FIG. 14 (Step S301).

At Step S301, the image converter 143a acquires the reflected-excitation-light image Pr of the observed region S at Step S101, and white-light images Pw1 and Pw2 of two frames that are sequential with the reflected-excitation-light image Pr interposed therebetween from the reflected-light image storage unit 41 sequentially in chronological order. The reflected-excitation-light image Pr, and the white-light images Pw1 and Pw2 of the observed region S are reflected-light images of the observed region S captured by the reflected-light imaging unit 36 at Step S101 illustrated in FIG. 7. In detail, as illustrated in FIG. 15, the white-light image Pw1 is the reflected-light image of the observed region S captured by the reflected-light imaging unit 36 at a timing T1 when the observed region S is irradiated with the white light. The reflected-excitation-light image Pr is the reflected-light image of the observed region S captured by the reflected-light imaging unit 36 at a timing T2 when the observed region S is irradiated with the excitation light after the timing T1. The white-light image Pw2 is the reflected-light image of the observed region S captured by the reflected-light imaging unit 36 at a timing T3 when the observed region S is irradiated with the white light again after the timing 12. The image converter 143a calculates a brightness signal of the white-light image Pw1 thus acquired, and performs gain adjustment process for making the brightness uniform on the brightness signal thus calculated to generate a brightness signal image corresponding to the white-light image Pw1, that is, a reference image serving as one of the motion vector calculation images. In the same manner, the image converter 143a calculates a brightness signal of the next white-light image Pw2 thus acquired, and performs the gain adjustment process for making the brightness uniform on the brightness signal thus calculated to generate a brightness signal image corresponding to the white-light image Pw2, that is, a target image serving as one of the motion vector calculation images.

The brightness signal Y for generating the motion vector calculation image is calculated using the pixel value R of the red component, the pixel value G of the green component, and the pixel value B of the blue component of the white-light images Pw1 and Pw2 of the observed region S by Equation: Brightness Signal $Y=0.29 \times R+0.6 \times G+0.11 \times B$. The image converter 143a, instead of calculating the brightness signal Y, may extract the pixel value of the R channel including many wavelength bands of the excitation light from the white-light images Pw1 and Pw2 of the observed region S alone, and perform the gain adjustment process on the pixel value of the R channel thus extracted to generate the motion vector calculation images (reference image and target image).

Subsequently, the motion vector calculator 143 sets the motion vector measurement blocks on the motion vector calculation image generated at Step S301 in the same manner as that of Step S202 in the first embodiment (refer to FIG. 8) (Step S302). The motion vector calculator 143 then calculates the motion vector information between the white-light images that are sequential in chronological order with the fluorescence image of the observed region S at Step S101 interposed therebetween (Step S303).

At Step S303, the motion vector calculation unit 143c acquires the motion vector calculation images at Step S302 (that is, the reference image and the target image corresponding to the white-light images Pw1 and Pw2, respectively), and the reflected-excitation-light image Pr between both of the motion vector images from the measurement block setting unit 43b sequentially in chronological order. The motion vector calculation unit 143c uses a known method, such as the block matching method, in the same manner as in the first embodiment to calculate the motion vector information between the reference image Pi corresponding to the white-light image Pw1, and the target image corresponding to the next white-light image Pw2. The motion vector calculation unit 143c calculates the motion vector information for all of the measurement blocks on the reference image, and performs averaging process of the motion vector information based on all the pieces of the motion vector information thus obtained to calculate representative motion vector information Va between the reference image and the target image.

The motion vector information Va calculated by the motion vector calculation unit 143c is motion vector information between the white-light images Pw1 and Pw2 at the timings T1 and T3, respectively, that are sequential in chronological order with the reflected-excitation-light image Pr at the timing T2 interposed therebetween. The reflected-excitation-light image Pr at the timing T2 is an image captured at the same timing as that of the fluorescence image Pf of the observed region S captured by the fluorescence imaging unit 37 as described above. In other words, the pixel positions with respect to the same object (e.g., the lesion K) in the reference image based on the reflected-excitation-light image Pr and the fluorescence image Pf coincide with each other. The motion vector calculation unit 143c calculates motion vector information Vb between the white-light image Pw1 at the timing T1 and the reflected-excitation-light image Pr at the timing T2 eventually by Equation (3) based on the motion vector information Va thus calculated, and imaging time intervals ΔT1 and ΔT2 of the first white-light image Pw1, the reflected-excitation-light image Pr, and the next white-light image Pw2 of the observed region S as described above. The imaging time interval ΔT1 is time difference (T2−T1) between the timing T2 at which the reflected-excitation-light image Pr is captured, and the timing T1 at which the white-light image Pw1 is captured. The imaging time interval ΔT2 is time difference (T3−T2) between the timing T3 at which the white-light image Pw2 is captured, and the timing T2 at which the reflected-excitation-light image Pr is captured.

$$Vb = Va \times \{\Delta T1/(\Delta T1+\Delta T2)\} \quad (3)$$

For example, if the white-light images Pw1 and Pw2, and the reflected-excitation-light image Pr are captured at the same time interval, the imaging time intervals ΔT1 and ΔT2 are the same value, and the motion vector information Vb between the white-light image Pw1 and the reflected-excitation-light image Pr is one-half of the motion vector information Va between the two white-light images Pw1 and Pw2. Thus, the motion vector information Vb calculated eventually by the motion vector calculation unit 143c is the motion vector information between the fluorescence image Pf of the observed region S at the same timing T2 as that of the reflected-excitation-light image Pr of the observed region S, and the white-light image Pw1 of the observed region S at the timing T1.

After the completion of the processing at Step S303, the motion vector calculator 143 returns to Step S102 illustrated in FIG. 7. Subsequently, the image processing apparatus 104 goes to Step S103 in the same manner as in the first embodiment, and performs the processing subsequent to Step S103.

The white-light image Pw1 and the fluorescence image Pf for which the motion vector information is specified are aligned with each other in the same manner as in the first embodiment, whereby the misalignment with respect to the same object such as the lesion K is corrected. Furthermore, the brightness of the fluorescence image Pf aligned with the white-light image Pw1 is normalized with high accuracy in the same manner as in the first embodiment, thereby correcting the intensity of the fluorescence in the fluorescence image Pf caused by differences in the distance from the observed region S serving as the object to the fluorescence imaging unit 37 precisely.

As described above, in the second embodiment of the present invention, the fluorescence image and the reflected-excitation-light image, and two white-light images that are sequential in chronological order with the reflected-excitation-light image interposed therebetween are captured for one observed region. Based on the motion vector information between the two white-light images, and the time intervals of the reflected-excitation-light image and the two white-light images, the motion vector information between the reflected-excitation-light image and the white-light image is calculated. Other components are the same as those in the first embodiments. Therefore, the same advantageous effects as those in the first embodiment can be achieved. In addition, even if pieces of image information of the white-light image and the reflected-excitation-light image are different from each other significantly because of the difference in the spectroscopic characteristics of the white-light image and the reflected-excitation-light image, the motion vector information between the white-light image and the fluorescence image of the observed region can be calculated accurately without being affected by the difference in the spectroscopic characteristics of the white-light image and the reflected-excitation-light image. As a result, it is possible to improve the accuracy of the normalization process of the fluorescence image more securely.

Third Embodiment

A third embodiment of the present invention will now be described. In the first embodiment, the fluorescence image of the observed region S is divided by the normalization image generated based on the white-light image of the observed region S, whereby the brightness of the fluorescence image is normalized. However, in the third embodiment, a brightness component image based on the reflected light (white light) from the observed region S is captured by the fluorescence imaging unit 37 at the same timing as that of the white-light image of the observed region S, and the fluorescence image of the observed region S is divided by the brightness component image, whereby the brightness of the fluorescence image is normalized.

Figure 16:
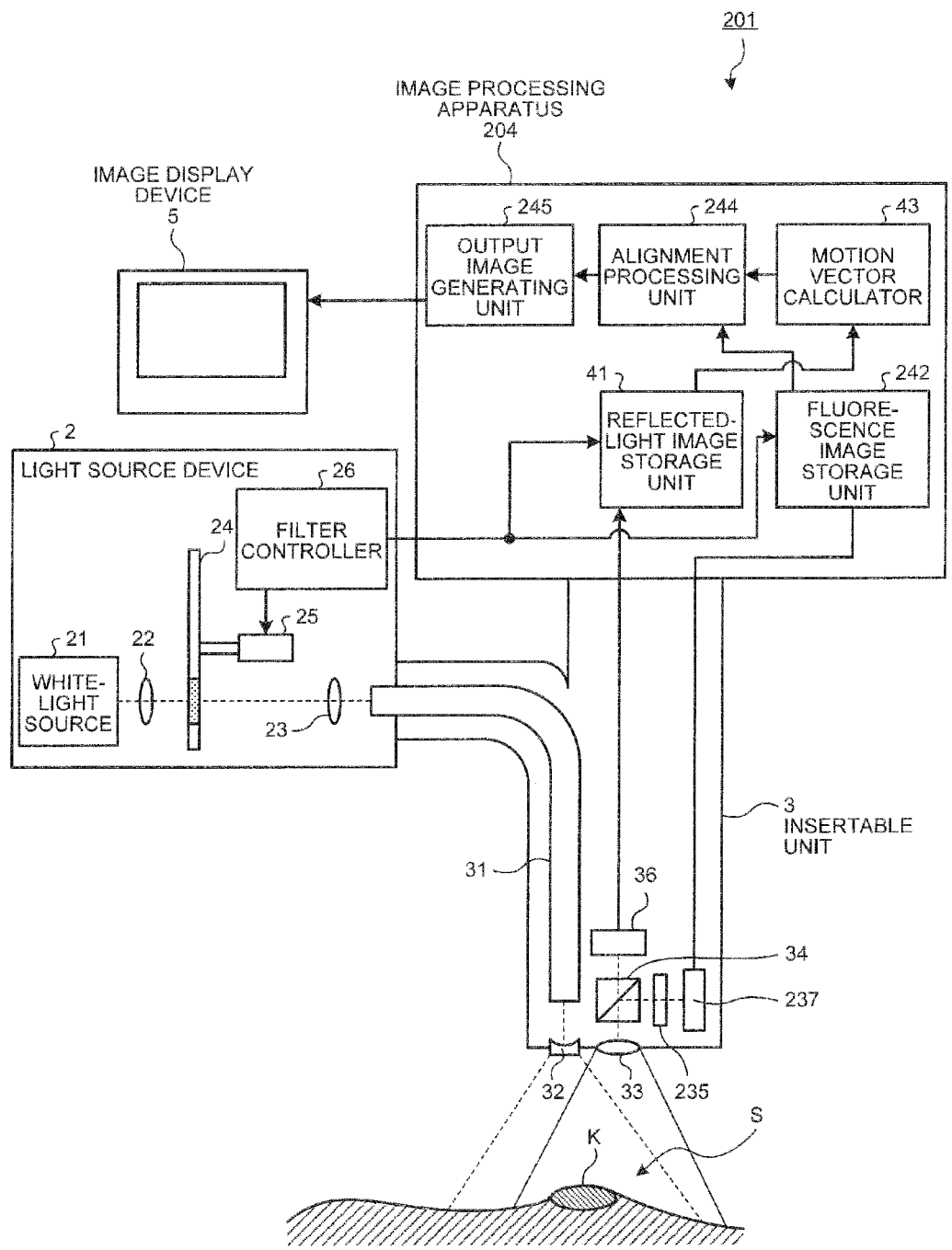
FIG. 16 is a block diagram schematically illustrating an exemplary configuration of an endoscope apparatus according to a third embodiment of the present invention.

FIG. 16 is a block diagram schematically illustrating an exemplary configuration of an endoscope apparatus according to the third embodiment of the present invention. As illustrated in FIG. 16, an endoscope apparatus 201 according to the third embodiment includes an image processing apparatus 204 instead of the image processing apparatus 4 of the endoscope apparatus 1 according to the first embodiment, a barrier filter 235 instead of the barrier filter 35, and a fluorescence imaging unit 237 instead of the fluorescence imaging unit 37. The image processing apparatus 204 according to the third embodiment includes a fluorescence image storage unit 242 instead of the fluorescence image storage unit 42 of the image processing apparatus 4 according to the first embodiment, an alignment processing unit 244 instead of the alignment processing unit 44, and an output image generating unit 245 instead of the output image generating unit 45. Other components are the same as those of the first embodiment, and the same reference numerals are assigned to the same components.

Figure 17:
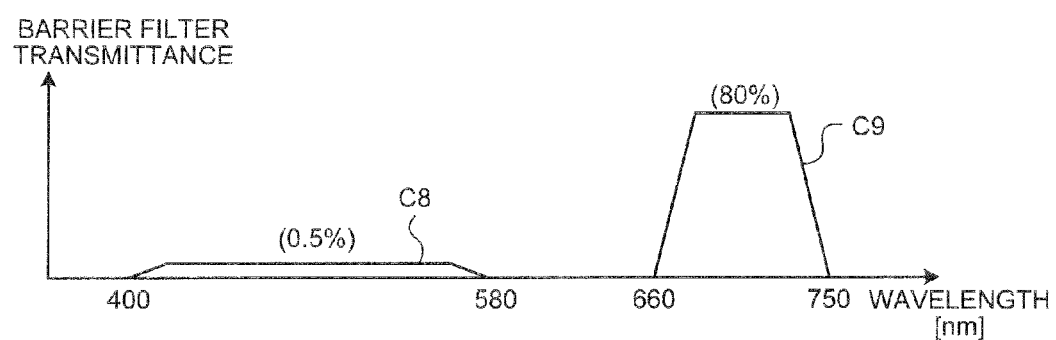
FIG. 17 is a schematic illustrating an example of transmittance characteristics of a barrier filter in the third embodiment of the present invention.

The barrier filter 235 is a filter for transmitting light at a wavelength band necessary for the fluorescence imaging unit 237, and blocking light at a wavelength band unnecessary for the fluorescence imaging unit 237 among the light from the observed region S separated into the optical path on the fluorescence imaging unit 237 side by the dichroic mirror 34. FIG. 17 is a schematic illustrating an example of transmittance characteristics of the barrier filter in the third embodiment of the present invention. As indicated by correlation lines C8 and C9 of transmittance versus wavelength illustrated in FIG. 17, the barrier filter 235 has transmittance characteristics that transmit light at a wavelength band of 400 to 580 nm, and light at a wavelength band of 660 to 750 nm. In detail, among the reflected light from the observed region S separated into the optical path on the fluorescence imaging unit 237 side by the dichroic mirror 34, the barrier filter 235 transmits the reflected light at a wavelength band of 400 to 580 nm, and blocks the reflected light at wavelength bands other than this wavelength band. Furthermore, among the fluorescence and the excitation light from the observed region S separated into the optical path on the fluorescence imaging unit 237 side by the dichroic mirror 34, the barrier filter 235 blocks the excitation light from the observed region S, and transmits the fluorescence from the observed region S, which is light at a wavelength band of 660 to 750 nm. Note that it is preferable that the transmittance of the reflected light at a wavelength band of 400 to 580 nm by the barrier filter 235 be approximately 0.5%, and that the transmittance of the light (fluorescence) at a wavelength band of 660 to 750 nm be approximately 80%.

The fluorescence imaging unit 237 is realized by using a monochrome imaging element having high sensitivity characteristics compared with the reflected-light imaging unit 36. The fluorescence imaging unit 237 receives the reflected light at a wavelength band of 400 to 580 nm passing through the barrier filter 235 among the white light reflected from the observed region S at a timing when the observed region S is irradiated with the white light. Thus, the fluorescence imaging unit 237 captures a reflected-light image (hereinafter, referred to as a brightness component image) of the observed region S based on the reflected light at a wavelength band of 400 to 580 nm at the same imaging timing as that of the white-light image of the observed region S by the reflected-light imaging unit 36. Every time the fluorescence imaging unit 237 captures the brightness component image of the observed region S, the fluorescence imaging unit 237 transmits an image signal including the image information thus obtained to the image processing apparatus 204 sequentially. Note that the fluorescence imaging unit 237 has the same functions as those of the fluorescence imaging unit 37 in the first embodiment other than the imaging function of the brightness component image.

The image processing apparatus 204 includes the reflected-light image storage unit 41 and the motion vector calculator 43, and further includes the fluorescence image storage unit 242 instead of the fluorescence image storage unit 42 of the image processing apparatus 4 according to the first embodiment, the alignment processing unit 244 instead of the alignment processing unit 44, and the output image generating unit 245 instead of the output image generating unit 45. In the image processing apparatus 204, the reflected-light image storage unit 41 performs interpolation process on the white-light image and the reflected-excitation-light image captured by the reflected-light imaging unit 36, and stores therein pieces of the image information of the white-light image and the reflected-excitation-light image thus interpolated. The image processing apparatus 204 has the same motion vector calculation process function as that of the image processing apparatus 4 according to the first embodiment.

The fluorescence image storage unit 242 stores therein the image information captured by the fluorescence imaging unit 237 based on the control of the filter controller 26 of the light source device 2. Specifically, the fluorescence image storage unit 242 acquires the filter information transmitted by the filter controller 26, and recognizes whether the filter of the rotating filter 24 actually positioned in the optical path in the light source device 2 is the white-light filter 24a or the excitation-light filter 24b based on the filter information thus acquired. If the filter positioned in the optical path in the light source device 2 is the white-light filter 24a, the fluorescence image storage unit 242 acquires the image information of the brightness component image of the observed region S from the fluorescence imaging unit 237 and stores therein the image information thus acquired sequentially. If the filter positioned in the optical path in the light source device 2 is the excitation-light filter 24b, the fluorescence image storage unit 242 acquires the image information of the fluorescence image of the observed region S from the fluorescence imaging unit 237 in the same manner as in the first embodiment, and stores therein the image information thus acquired sequentially.

The alignment processing unit 244 performs alignment process on the fluorescence image and the reflected-light image of the observed region S to correct misalignment of the object between the fluorescence image and the reflected-light image. Specifically, the alignment processing unit 244 sequentially reads pieces of the image information of the brightness component image and the fluorescence image of the observed region S captured by the fluorescence imaging unit 237 from the fluorescence image storage unit 242. Furthermore, the alignment processing unit 244 acquires the motion vector information calculated by the motion vector calculation unit 43c, that is, the motion vector information between the fluorescence image and the white-light image of the observed region S from the motion vector calculator 43. The alignment processing unit 244 performs the alignment process for aligning the pixel positions with respect to the same object (e.g., the lesion K) in the fluorescence image and the brightness component image of the observed region S based on the motion vector information thus acquired. In this manner, the alignment processing unit 244 corrects the misalignment of the object between the fluorescence image and the brightness component image. The alignment processing unit 244 transmits the pieces of the image information of the fluorescence image and the brightness component image thus aligned with each other to the output image generating unit 245.

The output image generating unit 245 generates an output image to be displayed on the image display device 5 based on the pieces of the image information aligned with each other by the alignment processing unit 244. Specifically, the output image generating unit 245 acquires the pieces of the image information of the fluorescence image and the brightness component image of the observed region S thus aligned with each other from the alignment processing unit 244. The output image generating unit 245 normalizes the brightness of the fluorescence image based on the brightness of the brightness component image thus acquired to generate a normalized fluorescence image of the observed region S. In this case, the output image generating unit 245 uses the brightness component image acquired from the alignment processing unit 244 as the normalization image for normalizing the fluorescence image. The output image generating unit 245 divides the brightness value of the fluorescence image on which the alignment process is performed by the brightness value of the brightness component image. In this manner, the output image generating unit 245 normalizes the brightness value of each pixel of the fluorescence image of the observed region S, and as a result, generates a normalized fluorescence image of the observed region S. Note that the output image generating unit 245 has the same functions as those of the output image generating unit 45 of the image processing apparatus 4 according to the first embodiment other than the normalization process function of the fluorescence image.

Figure 18:
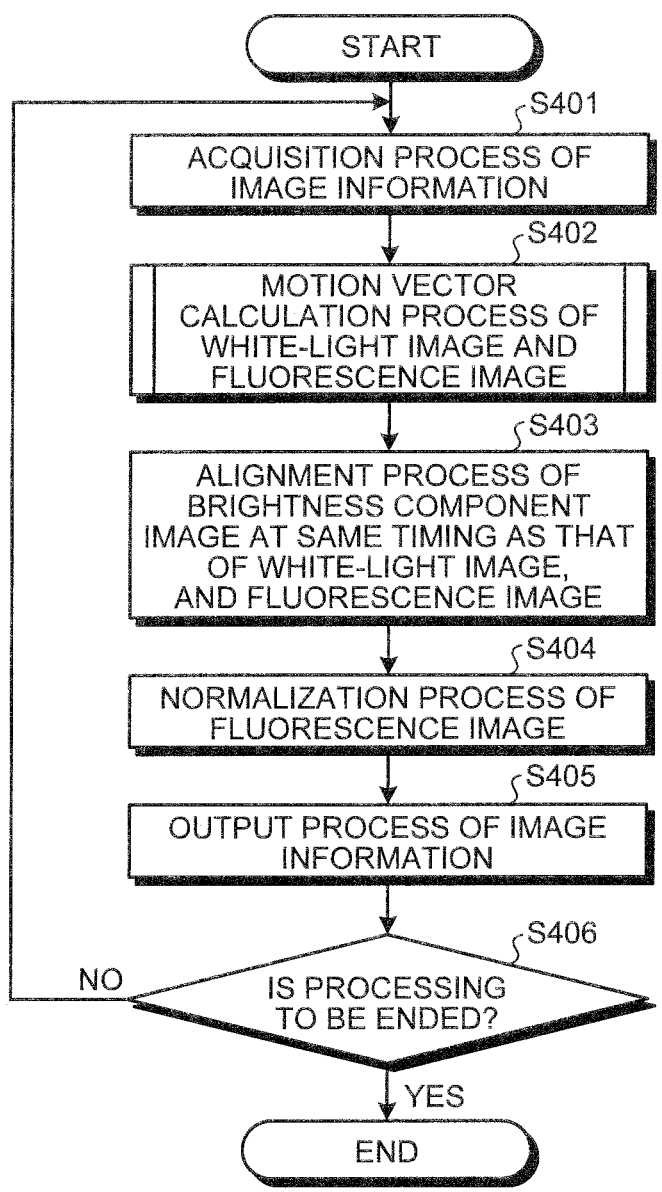
FIG. 18 is a flowchart exemplifying processing of the image processing apparatus according to the third embodiment of the present invention.
Figure 19:
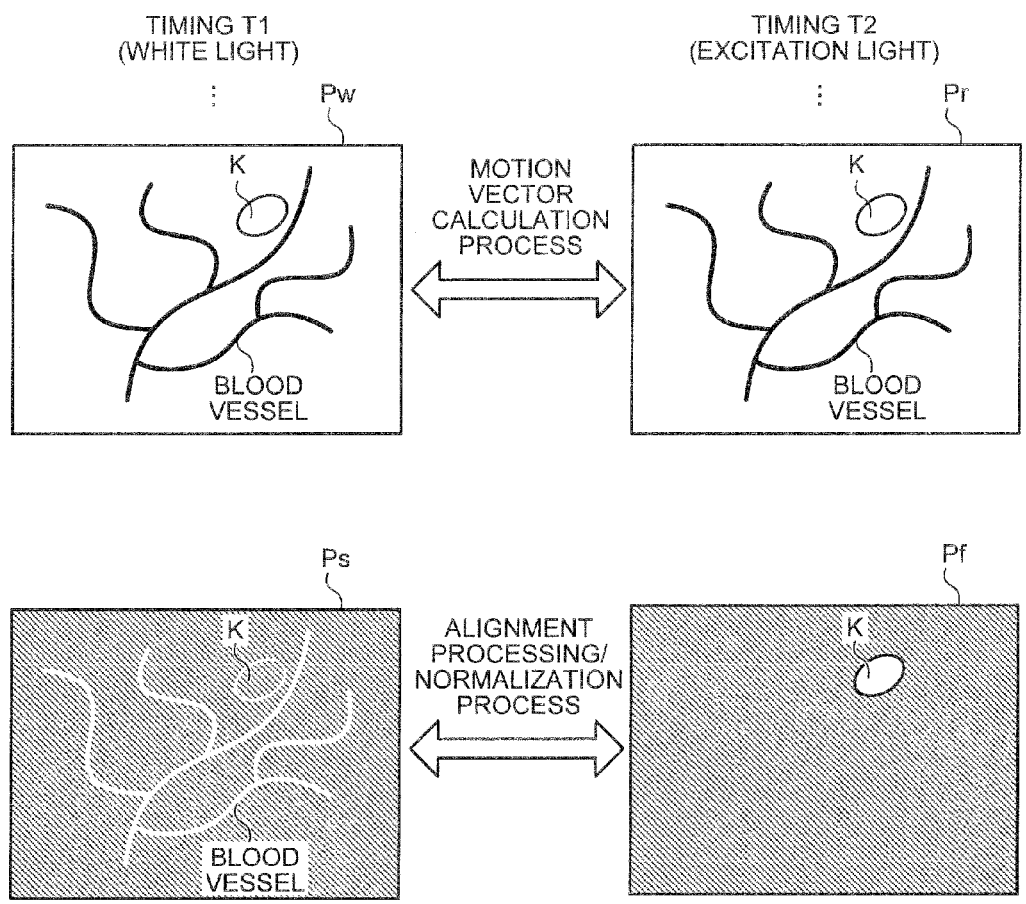
FIG. 19 is a schematic for specifically explaining alignment process and normalization process of a fluorescence image of an observed region in the third embodiment.

Operations performed by the image processing apparatus 204 according to the third embodiment of the present invention will now be described. FIG. 18 is a flowchart exemplifying processing of the image processing apparatus according to the third embodiment of the present invention. FIG. 19 is a schematic for specifically explaining the alignment process and the normalization process of the fluorescence image of the observed region in the third embodiment. The operations performed by the image processing apparatus 204 according to the third embodiment will now be described below with reference to FIGS. 18 and 19.

As illustrated in FIG. 18, the image processing apparatus 204 acquires the image information of the observed region S (Step S401). At Step S401, in the same manner as that of Step S101, the reflected-light image storage unit 41 acquires the white-light image Pw of the observed region S captured by the reflected-light imaging unit 36 at the timing T1 when the observed region S is irradiated with the white light, and the reflected-excitation-light image Pr of the observed region S captured by the reflected-light imaging unit 36 at the timing 12 when the observed region S is irradiated with the excitation light sequentially, and stores therein the white-light image Pw and the reflected-excitation-light image Pr as color image information of the observed region S. By contrast, the fluorescence image storage unit 242 acquires a brightness component image Ps of the observed region S captured by the fluorescence imaging unit 237 at the same imaging timing as that of the white-light image Pw, that is, at the timing T1, and stores therein the brightness component image Ps thus acquired as monochrome reflected-light image information. Furthermore, the fluorescence image storage unit 242 acquires the fluorescence image Pf of the observed region S captured by the fluorescence imaging unit 237 at the same imaging timing as that of the reflected-excitation-light image Pr, that is, at the timing 12, and stores therein the fluorescence image Pf thus acquired as monochrome image information.

Subsequently, in the same manner as that of Step S101 illustrated in FIG. 7, the image processing apparatus 204 calculates the motion vector information between the white-light image Pw and the fluorescence image Pf of the observed region S at Step S401 (Step S402). The image processing apparatus 204 performs alignment process on the brightness component image Ps at the same timing T1 as that of the white-light image Pw, and the fluorescence image Pf (Step S403). Note that, at Step S402, the motion vector calculator 43 of the image processing apparatus 204 performs the processing of Steps S201 to S203 illustrated in FIG. 8.

At Step S403, the alignment processing unit 244 acquires the brightness component image Ps and the fluorescence image Pf of the observed region S at Step S401 from the fluorescence image storage unit 242. Furthermore, the alignment processing unit 244 acquires the motion vector information between the white-light image Pw and the reflected-excitation-light image Pr calculated by the motion vector calculator 43 at Step S402, that is, the motion vector information between the white-light image Pw and the fluorescence image Pf. The white-light image Pw and the brightness component image Ps are image information of the observed region S captured at the same timing T1, and the pixel positions with respect to the same object (e.g., the lesion K) in the white-light image Pw and the brightness component image Ps coincide with each other. The reflected-excitation-light image Pr and the fluorescence image Pf are image information of the observed region S captured at the same timing T2, and the pixel positions with respect to the same object (e.g., the lesion K) in the reflected-excitation-light image Pr and the fluorescence image Pf coincide with each other. Therefore, the motion vector information between the white-light image Pw and the fluorescence image Pf acquired by the alignment processing unit 244 from the motion vector calculator 43 corresponds to the motion vector information between the brightness component image Ps and the fluorescence image Pf of the observed region S. The alignment processing unit 244 performs the alignment process for aligning the pixel positions with respect to the same object in the brightness component image Ps and the fluorescence image Pf of the observed region S based on the motion vector information acquired from the motion vector calculator 43. In this manner, the alignment processing unit 244 corrects the misalignment of the object between the brightness component image Ps and the fluorescence image Pf (e.g., misalignment of the lesion K between both of the images).

Subsequently, the image processing apparatus 204 performs normalization process on the fluorescence image Pf of the observed region S on which the alignment process is performed at Step S403 (Step S404). At Step S404, the output image generating unit 245 acquires the brightness component image Ps and the fluorescence image Pf of the observed region S aligned with each other at Step S403 from the alignment processing unit 244. The output image generating unit 245 performs the normalization process on the fluorescence image Pf using the brightness component image Ps thus acquired as a normalization image. In other words, the output image generating unit 245 divides the brightness value of the fluorescence image Pf on which the alignment process is performed by the brightness value of the brightness component image Ps thus acquired, thereby normalizing the brightness value of each pixel of the fluorescence image Pf. In this manner, the output image generating unit 245 achieves the normalization process of the fluorescence image Pf of the observed region S.

The image processing apparatus 204 then, in the same manner as that of Step S105 illustrated in FIG. 7, performs the output process of the image information of the observed region S to be displayed on the image display device 5 (Step S405). Subsequently, in the same manner as that of Step S106 illustrated in FIG. 7, if a processing end operation such as an OFF operation is performed (YES at Step S406), the image processing apparatus 204 ends the processing. By contrast, the processing end operation is not performed yet (NO at Step S406), the image processing apparatus 204 returns to Step S401, and repeats the processing subsequent to Step S401.

As described above, in the third embodiment of the present invention, the white-light image and the brightness component image of the observed region are captured at the timing when the observed region is irradiated with the white light. The misalignment of the object between the brightness component image and the fluorescence image of the observed region is corrected based on the motion vector information between the white-light image and the reflected-excitation-light image of the observed region. The brightness value of the fluorescence image is divided by the brightness component image thus corrected, whereby the brightness of the fluorescence image is normalized. Other components are the same as those in the first embodiment. Therefore, the same advantageous effects as those in the first embodiment can be achieved. In addition, it is possible to facilitate normalizing the brightness of the fluorescence image based on the brightness signal of the brightness component image captured at the same timing as that of the white-light image of the observed region without generating a normalization image by calculating the brightness signal of the white-light image of the observed region. As a result, it is possible to reduce a load for the image processing apparatus when the normalization process of the fluorescence image is performed, and to shorten the processing time.

Fourth Embodiment

A fourth embodiment of the present invention will now be described. In the third embodiment, in the same manner as in the first embodiment, to calculate the motion vector information between the fluorescence image of the observed region S and the reflected-light image of the observed region S, the motion vector information between the reflected-excitation-light image of the observed region captured at the same timing as that of the fluorescence image, and the white-light image of the observed region S is calculated. However, in the fourth embodiment, in the same manner as in the second embodiment, to calculate the motion vector information between the fluorescence image of the observed region S and the reflected-light image of the observed region S, the motion vector information between two white-light images of the observed region S that are sequential in chronological order with the fluorescence image interposed therebetween. In other words, the invention according to the fourth embodiment is an arbitrary combination of the second embodiment and the third embodiment.

Figure 20:
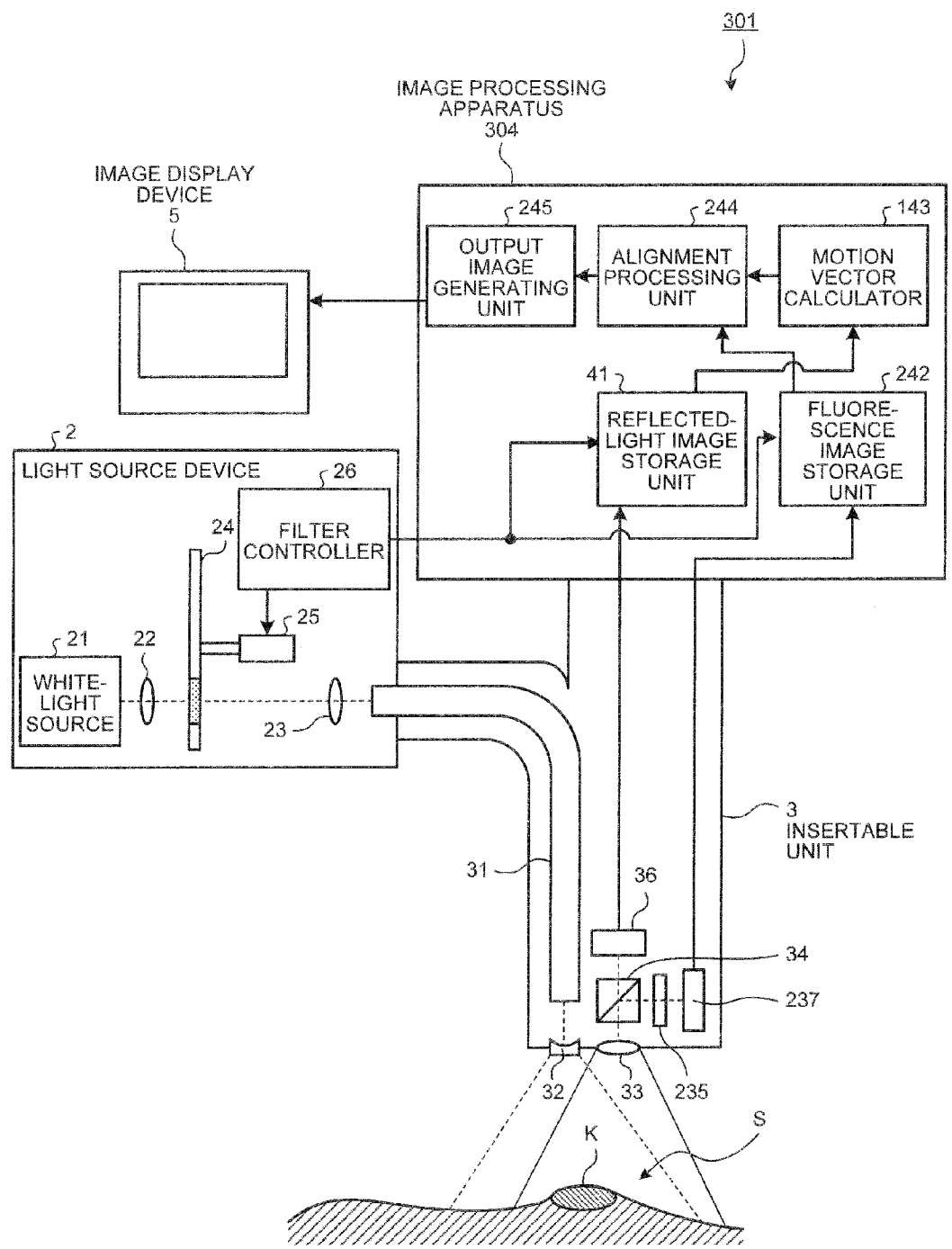
FIG. 20 is a block diagram schematically illustrating an exemplary configuration of an endoscope apparatus according to a fourth embodiment of the present invention.

FIG. 20 is a block diagram schematically illustrating an exemplary configuration of an endoscope apparatus according to the fourth embodiment of the present invention. As illustrated in FIG. 20, an endoscope apparatus 301 according to the fourth embodiment includes an image processing apparatus 304 instead of the image processing apparatus 204 of the endoscope apparatus 201 according to the third embodiment. Furthermore, the image processing apparatus 304 according to the fourth embodiment includes the motion vector calculator 143 in the second embodiment instead of the motion vector calculator 43 of the image processing apparatus 204 according to the third embodiment. Other components are the same as those in the third embodiment, and the same reference numerals are assigned to the same components.

The image processing apparatus 304 includes the reflected-light image storage unit 41, the fluorescence image storage unit 242, the alignment processing unit 244, and the output image generating unit 245, and further includes the motion vector calculator 143 instead of the motion vector calculator 43 of the image processing apparatus 204 according to the third embodiment. In the image processing apparatus 304, the reflected-light image storage unit 41 stores therein the reflected-excitation-light image and the white-light image of the observed region S captured consecutively in chronological order by the reflected-light imaging unit 36 sequentially. Specifically, the reflected-light image storage unit 41 stores therein the reflected-excitation-light image of one frame, and the white-light images of two frames that are sequential in chronological order with the reflected-excitation-light image interposed therebetween as color image information for one observed region S sequentially. By contrast, the motion vector calculator 143 functions in the same manner as in the second embodiment. Note that the image processing apparatus 304 has the same functions as those of the image processing apparatus 204 according to the third embodiment other than the functions of the reflected-light image storage unit 41 and the motion vector calculator 143.

Operations performed by the image processing apparatus 304 according to the fourth embodiment of the present invention will now be described. FIG. 21 is a schematic for specifically explaining the operations performed by the image processing apparatus according to the fourth embodiment. The image processing apparatus 304 according to the fourth embodiment performs the motion vector calculation process in the same manner as in the second embodiment, and operates in nearly the same manner as that of the image processing apparatus 204 according to the third embodiment other than the motion vector calculation process. In other words, the image processing apparatus 304 performs the processing nearly the same as Steps S401 to S406 illustrated in FIG. 18. At Step S402, the image processing apparatus 304 performs the processing of Steps S301 to S303 illustrated in FIG. 14. The operations performed by the image processing apparatus 304 will be specifically described below with reference to FIG. 21.

Specifically, as Step S401, the image processing apparatus 304 acquires the white-light image Pw1 of the observed region S captured by the reflected-light imaging unit 36, and a brightness component image Ps1 of the observed region S captured by the fluorescence imaging unit 237 at the timing T1 when the observed region S is irradiated with the white light. The image processing apparatus 304 then acquires the reflected-excitation-light image Pr of the observed region S captured by the reflected-light imaging unit 36, and the fluorescence image Pf of the observed region S captured by the fluorescence imaging unit 237 at the timing T2 when the observed region S is irradiated with the excitation light. Subsequently, the image processing apparatus 304 acquires the white-light image Pw2 of the observed region S captured by the reflected-light imaging unit 36, and a brightness component image Ps2 of the observed region S captured by the fluorescence imaging unit 237 at the timing T3 when the observed region S is irradiated with the white light again.

At Step S401, the reflected-light image storage unit 41 stores therein the reflected-excitation-light image Pr of the observed region S, and the two white-light images Pw1 and Pw2 thereof that are sequential in chronological order with the reflected-excitation-light image Pr interposed therebetween sequentially in chronological order. The fluorescence image storage unit 242 stores therein the brightness component image Ps1 at the same imaging timing as that of the white-light image Pw1, the fluorescence image Pf at the same imaging timing as that of the reflected-excitation-light image Pr, and the brightness component image Ps2 at the same imaging timing as that of the next white-light image Pw2 sequentially in chronological order.

By contrast, at Step S402, the image processing apparatus 304 performs the motion vector calculation process in the same manner as in the second embodiment. In other words, the motion vector calculator 143 of the image processing apparatus 304 performs the processing of Steps S301 to S303 illustrated in FIG. 14. As illustrated in FIG. 15, the motion vector calculator 143 calculates the motion vector information Va between the white-light image Pw1 at the timing T1 and the white-light image Pw2 at the timing T3. Based on the motion vector information Va thus calculated, and the imaging time intervals $\Delta T1$ and $\Delta T2$, the motion vector calculator 143 calculates the motion vector information Vb between the white-light image Pw1 at the timing T1 and the reflected-excitation-light image Pr at the timing T2 eventually by Equation (3). As described above, the motion vector information Vb is the motion vector information between the fluorescence image Pf of the observed region S at the same timing T2 as that of the reflected-excitation-light image Pr of the observed region S, and the white-light image Pw1 of the observed region S at the timing T1.

Subsequently, in the same manner as in the third embodiment, the image processing apparatus 304 goes to Step S403, and performs the processing subsequent to Step S403. In this case, as illustrated in FIG. 21, the alignment processing unit 244 performs the alignment process on the brightness component image Ps1 at the timing T1 and the fluorescence image Pf at the timing T2. The output image generating unit 245 divides the fluorescence image Pf by the brightness component image Ps1 on which the alignment process is performed to normalize the brightness of the fluorescence image Pf.

In the image processing apparatus 304 according to the fourth embodiment, the motion vector calculator 143 may calculate the motion vector information Vb between the white-light image Pw2 at the timing T3 and the reflected-excitation-light image Pr at the timing T2 eventually by Equation (4) based on the motion vector information Va, and the imaging time intervals $\Delta T1$ and $\Delta T2$.

$$Vb = Va \times \{\Delta T2/(\Delta T1 + \Delta T2)\} \qquad (4)$$

Note that the motion vector information Vb in this case is motion vector information between the fluorescence image Pf of the observed region S at the same timing T2 as that of the reflected-excitation-light image Pr of the observed region S, and the white-light image Pw2 of the observed region S at the timing T3.

The alignment processing unit 244 may perform the alignment process on the brightness component image Ps2 at the timing T3 and the fluorescence image Pf at the timing 12 based on the motion vector information Vb by Equation (4). Furthermore, the output image generating unit 245 may divide the fluorescence image Pf by the brightness component image Ps2 on which the alignment process is performed to normalize the brightness of the fluorescence image Pf.

As described above, in the fourth embodiment of the present invention, the fluorescence image and the reflected-excitation-light image, and two white-light images that are sequential in chronological order with the reflected-excitation-light image interposed therebetween are captured for one observed region. Based on the motion vector information between the two white-light images, and the time intervals of the reflected-excitation-light image and the two white-light images, the motion vector information between the reflected-excitation-light image and the white-light image is calculated. Other components are the same as those in the third embodiment. Therefore, the same advantageous effects as those in the second embodiment can be achieved, and the same advantageous effects as those in the third embodiment can be achieved as well.

In the first to fourth embodiments, the processing of the image processing apparatus performed by hardware is explained. However, it is not limited thereto, and the image processing apparatus according to the present invention may perform the processing by software. In other words, the image processing apparatuses 4, 104, 204, and 304 according to the first to fourth embodiments are realized by using a computer including a storage unit that stores therein a processing program, a CPU that executes the processing program in the storage unit, and the like, and each component in the image processing apparatus may operate in accordance with the processing program.

Specifically, the image processing apparatus 4 according to the first embodiment may perform the processing of Steps S101 to S106 based on the processing program, and perform the processing of Steps S201 to S203 at Step S102. The image processing apparatus 104 according to the second embodiment may perform the processing of Steps S101 to S106 based on the processing program, and perform the processing of Steps S301 to S303 at Step S102. The image processing apparatus 204 according to the third embodiment may perform the processing of Steps S401 to S406 based on the processing program, and perform the processing of Steps S201 to S203 at Step S402. The image processing apparatus 304 according to the fourth embodiment may perform the processing of Steps S401 to S406 based on the processing program, and perform the processing of Steps S301 to S303 at Step S402.

By contrast, in the first to fourth embodiments, the observed region S is irradiated with the white light, whereby the white-light image of the observed region S is captured. However, it is not limited thereto, and the observed region S may be irradiated with monochromatic light such as R light instead of the white light, whereby a monochromatic-light image based on the monochromatic light reflected from the observed region S may be captured. In this case, instead of the white light of the observed region S, motion vector information between the monochromatic-light image and the fluorescence image of the observed region S may be calculated, and misalignment of the object between the monochromatic-light image and the fluorescence image may be corrected based on the motion vector information thus calculated. The fluorescence image may be divided by the monochromatic-light image thus corrected, thereby normalizing the brightness of the fluorescence image.

In the first and the second embodiments, the brightness signal of the white-light image of the observed region S is calculated, and the normalization image is generated based on the brightness signal thus calculated. However, it is not limited thereto, and a signal value of a predetermined color (e.g., the R channel) of the white-light image or the monochromatic-light image of the observed region S may be calculated, and the normalization image may be generated based on the signal value of the predetermined color thus calculated.

In the second and the fourth embodiments, the motion vector information between two white-light images that are sequential in chronological order with the reflected-excitation-light image interposed therebetween is calculated sequentially every time the white-light image is captured. However, it is not limited thereto, and if the reflected-excitation-light image and the white-light image of the observed region are captured sequentially at constant time intervals, motion vector information between the first white-light image and the reflected-excitation-light image subsequent thereto of the observed region S may be calculated once, and the motion vector information thus calculated may be used as motion vector information between the next white-light image and the reflected-excitation-light image of the observed region S.

In the first to fourth embodiments, the rotating filter 24 that switches the white-light filter 24a and the excitation-light filter 24b sequentially is housed in the light source device 2, and the white light through the white-light filter 24a and the excitation light through the excitation-light filter 24b are output from the light source device 2 sequentially. However, it is not limited thereto, and the rotating filter 24 of the light source device 2 may be a filter provided with three or more types of filters including the white-light filter 24a and the excitation-light filter 24b. In this case, the rotating filter 24 may switch the white-light filter 24a, the excitation-light filter 24b, and the other filters (not illustrated) sequentially at time intervals specified in advance based on the control of the filter controller 26. This allows the light source device 2 to irradiate the observed region S with additional light at a desired wavelength band, such as monochromatic light of a desired color including the R light, in addition to the white light and the excitation light. Thus, the image processing apparatus according to the present invention can further acquire image information based on the additional light, and use the image information as a normalization image, thereby facilitating the normalization process of the fluorescence image of the observed region S. If such additional image information is acquired, motion vector information between the additional image information and the white-light image or the fluorescence image of the observed region S may be calculated, and the alignment process may be performed on the pieces of the image information to superimpose the additional image information and the white-light image or the fluorescence image.

In the first to fourth embodiments, the endoscope apparatus for observing an inside of a body cavity of a subject such as a patient is explained as an example of the imaging apparatus according to the present invention. However, it is not limited thereto, and the imaging apparatus according to the present invention may be an endoscope apparatus used in a field other than the medical field, be an imaging apparatus other than the endoscope apparatus, such as a digital camera and a digital video camera, or be a portable information terminal, such as a cell phone having an imaging function. Furthermore, the image processing apparatus according to the present invention is not limited to an apparatus provided to the endoscope apparatus for medical use described above, and may be an apparatus provided to any one of an endoscope apparatus used in a field other than the medical field, an imaging apparatus other than the endoscope apparatus, such as a digital camera and a digital video camera, and a portable information terminal, such as a cell phone having an imaging function.

In the first to fourth embodiments, the output image generating unit functions as an image generating unit that normalizes the brightness of the fluorescence image of the observed region on which the alignment process is performed by the alignment processing unit, and that generates the normalized fluorescence image of the observed region. However, it is not limited thereto, and the output image generating unit may function as an image generating unit that generates an output image obtained by superimposing a fluorescence object in the fluorescence image of the observed region, and the same object as the fluorescence object in the reflected-light image of the observed region without normalizing the fluorescence image of the observed region.

Specifically, the output image generating unit 45 in the first and the second embodiments acquires the pieces of the image information of the fluorescence image and the white-light image of the observed region S aligned with each other from the alignment processing unit 44, and superimposes the same object (e.g., the lesion K) in the fluorescence image and the white-light image aligned with each other and thus acquired, thereby generating the superimposed image of the fluorescence image and the white-light image obtained by superimposing the same object therein as output image information. In this case, at Step S104 illustrated in FIG. 7, the output image generating unit 45 performs the superimposition process for superimposing the same object (e.g., the lesion K) in the fluorescence image and the white-light image thus aligned with each other instead of the normalization process of the fluorescence image. Subsequently, at Step S105 illustrated in FIG. 7, the output image generating unit 45 generates the superimposed image of the fluorescence image and the white-light image aligned with each other. The output image generating unit 45 transmits the superimposed image of the observed region S thus generated to the image display device 5 to cause the image display device 5 to display the superimposed image of the observed region S.

In the same manner as in the first and the second embodiments, an image processing apparatus including the output image generating unit 45 that generates such a superimposed image can calculate motion vector information between a fluorescence image that includes little shape information and a white-light image. Base on the motion vector information thus calculated, the image processing apparatus can correct misalignment of an object between the fluorescence image and the white-light image of an observed region with high accuracy, and superimpose the same object in the fluorescence image and the white-light image of the observed region precisely. This makes it possible to prevent the misalignment between an abnormal tissue such as a lesion in the fluorescence image, and the same abnormal tissue in the white-light image from occurring. As a result, the same advantageous effects as those in the first and the second embodiments can be achieved. In addition, it is possible to facilitate fluorescence observation of the observed region in the fluorescence image, and to realize an image processing apparatus, an imaging apparatus, an image processing program, and an image processing method that can improve detectability of an abnormal tissue in a subject with the fluorescence image of the observed region.

By contrast, the output image generating unit 245 in the third and the fourth embodiments acquires the pieces of the image information of the fluorescence image and the brightness component image of the observed region S thus aligned with each other, and the image information of the white-light image of the observed region S from the alignment processing unit 244. Based on the alignment process result of the fluorescence image and the brightness component image thus acquired, the output image generating unit 245 superimposes the same object (e.g., the lesion K) in the fluorescence image and the white-light image of the observed region S. In other words, the output image generating unit 245 superimposes the same object in the white-light image of the observed region S captured at the same timing as that of the brightness component image thus acquired, and in the fluorescence image on which the alignment process is performed. The output image generating unit 245 generates the superimposed image of the fluorescence image and the white-light image obtained by superimposing the same object therein by the superimposition process as output image information. In this case, at Step S404 illustrated in FIG. 18, the output image generating unit 245 performs the superimposition process for superimposing the same object (e.g., the lesion K) in the fluorescence image thus aligned with the brightness component image, and in the white-light image at the same imaging timing as that of the brightness component image instead of the normalization process of the fluorescence image. Subsequently, at Step S405 illustrated in FIG. 18, the output image generating unit 245 generates the superimposed image of the fluorescence image on which the alignment process is performed and the white-light image. The output image generating unit 45 transmits the superimposed image of the observed region S thus generated to the image display device 5 to cause the image display device 5 to display the superimposed image of the observed region S.

In the same manner as in the third and the fourth embodiments, an image processing apparatus including the output image generating unit 245 that generates such a superimposed image can calculate motion vector information between a fluorescence image that includes little shape information and a white-light image. Base on the motion vector information thus calculated, the image processing apparatus can correct misalignment of an object between the fluorescence image and the white-light image of an observed region with high accuracy, and superimpose the same object in the fluorescence image and the white-light image of the observed region precisely. This makes it possible to prevent the misalignment between an abnormal tissue such as a lesion in the fluorescence image and the same abnormal tissue in the white-light image from occurring. As a result, the same advantageous effects as those in the third and the fourth embodiments can be achieved. In addition, it is possible to facilitate fluorescence observation of the observed region in the fluorescence image, and to realize an image processing apparatus, an imaging apparatus, an image processing program, and an image processing method that can improve detectability of an abnormal tissue in a subject with the fluorescence image of the observed region.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
   a motion vector calculator that calculates motion vector information between a reflected-excitation-light image of an observed region based on excitation light, and a reflected-light image of the observed region based on reflected light from the observed region; and
   an alignment processing unit that corrects misalignment of an object between a fluorescence image and the reflected-light image based on the motion vector information.

2. The image processing apparatus according to claim 1, further comprising an image generating unit that normalizes brightness of the fluorescence image in which the misalignment of the object is corrected, and generates a normalization fluorescence image of the observed region.

3. The image processing apparatus according to claim 1, further comprising an image generating unit that generates an output image in which a fluorescence object in the fluorescence image and an object same as the fluorescence object in the reflected-light image are superimposed.

4. The image processing apparatus according to claim 1, wherein
   the fluorescence image and the reflected-light image are captured alternately at time intervals specified in advance, and
   the motion vector calculator calculates motion vector information between two of such reflected-light images of the observed region that are sequential in chronological order with the fluorescence image interposed therebetween, and calculates motion vector information between the fluorescence image and the reflected-light image based on the motion vector information thus calculated and the time intervals.

5. The image processing apparatus according to claim 2, wherein
   the alignment processing unit aligns pixel positions in the fluorescence image and the reflected-light image based on the motion vector information, and
   the image generating unit divides a brightness value of the fluorescence image by a brightness value of the reflected-light image in which the pixel positions are aligned with those in the fluorescence image, and generates the normalization fluorescence image.

6. The image processing apparatus according to claim 2, wherein
   the alignment processing unit acquires a brightness component image of the observed region captured at a timing same as that of the reflected-light image, and aligns pixel positions in the brightness component image and the fluorescence image based on the motion vector information, and
   the image generating unit divides a brightness value of the fluorescence image by a brightness value of the brightness component image in which the pixel positions are aligned with those in the fluorescence image, and generates the normalization fluorescence image.

7. The image processing apparatus according to claim 3, wherein
   the alignment processing unit acquires a brightness component image of the observed region captured at a timing same as that of the reflected-light image, and aligns pixel positions in the brightness component image and the fluorescence image based on the motion vector information, and
   the image generating unit superimposes the fluorescence object in the fluorescence image and the object same as the fluorescence object in the reflected-light image captured at a timing same as that of the brightness component image in which the pixel positions are aligned with those in the fluorescence image, and generates the output image.

8. The image processing apparatus according to claim 2, wherein the image generating unit, correspondingly to a signal value of a pixel of a fluorescence object in the fluorescence image, performs desired color conversion processing on a signal value of a pixel of an object same as the fluorescence object in the reflected-light image, and superimposes the reflected-light image and the fluorescence image.

9. The image processing apparatus according to claim 3, wherein the image generating unit, correspondingly to a signal value of a pixel of a fluorescence object in the fluorescence image, performs desired color conversion processing on a signal value of a pixel of an object same as the fluorescence object in the reflected-light image, and superimposes the reflected-light image and the fluorescence image.

10. The image processing apparatus according to claim 1, wherein the reflected-light image is a monochromatic-light image or a white-light image of the observed region.

11. An imaging apparatus comprising:
    a light source unit that switches normal light and excitation light, and irradiates an observed region therewith;
    a reflected-light imaging unit that receives reflected light from the observed region irradiated with the normal light, and captures a reflected-light image of the observed region;
    a fluorescence imaging unit that receives fluorescence generated from the observed region irradiated with the excitation light, and captures a fluorescence image of the observed region;
    a motion vector calculator that calculates motion vector information between a reflected-excitation-light image of the observed region and the reflected-light image of the observed region; and
    an alignment processing unit that corrects misalignment of an object between the fluorescence image and the reflected-light image based on the motion vector information.

12. A computer-readable storage device with an executable program stored thereon, wherein the program instructs a processor to perform:
- calculating motion vector information between a reflected-excitation-light image of an observed region based on excitation light, and a reflected-light image of the observed region based on reflected light from the observed region; and
- correcting misalignment of an object between a fluorescence image and the reflected-light image based on the motion vector information.

13. An image processing method comprising:
- calculating motion vector information between a reflected-excitation-light image of an observed region based on excitation light, and a reflected-light image of the observed region based on reflected light from the observed region; and
- correcting misalignment of an object between a fluorescence image and the reflected-light image based on the motion vector information.

* * * * *